US011674029B2

(12) United States Patent
Perry et al.

(10) Patent No.: US 11,674,029 B2
(45) Date of Patent: *Jun. 13, 2023

(54) LUBRICIOUS STRUCTURES, METHODS OF MAKING THEM, AND METHODS OF USE

(71) Applicant: University of Florida Research Foundation, Inc., Gainesville, FL (US)

(72) Inventors: Scott S. Perry, Houston, TX (US); Alexander Rudy, Ocoee, FL (US); Wallace Gregory Sawyer, Gainesville, FL (US); Thomas Ettor Angelini, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 180 days.

This patent is subject to a terminal disclaimer.

(21) Appl. No.: 17/166,671

(22) Filed: Feb. 3, 2021

(65) Prior Publication Data

US 2021/0171758 A1 Jun. 10, 2021

Related U.S. Application Data

(63) Continuation of application No. 16/327,526, filed as application No. PCT/US2017/048649 on Aug. 25, 2017, now Pat. No. 11,066,545.

(60) Provisional application No. 62/379,478, filed on Aug. 25, 2016.

(51) Int. Cl.
*C08L 33/26* (2006.01)
*A61L 29/14* (2006.01)
*A61L 29/06* (2006.01)
*A61L 29/08* (2006.01)
*C08L 33/02* (2006.01)
*C08L 33/08* (2006.01)
*C08L 83/04* (2006.01)

(52) U.S. Cl.
CPC .............. *C08L 33/26* (2013.01); *A61L 29/06* (2013.01); *A61L 29/085* (2013.01); *A61L 29/14* (2013.01); *C08L 33/02* (2013.01); *C08L 33/08* (2013.01); *C08L 83/04* (2013.01); *A61L 2400/10* (2013.01); *C08L 2203/02* (2013.01)

(58) Field of Classification Search
CPC ........ A61L 29/14; A61L 29/06; A61L 29/085; A61L 2400/10; C08L 33/26; C08L 33/02; C08L 33/08; C08L 83/04; C08L 2203/02
See application file for complete search history.

(56) References Cited

U.S. PATENT DOCUMENTS

| 5,804,318 A | 9/1998 | Pinchuk et al. |
| 6,169,127 B1 | 1/2001 | Lohmann et al. |
| 6,835,410 B2 | 12/2004 | Chabrecek et al. |
| 7,019,082 B2 | 3/2006 | Matyjaszewski et al. |
| 11,066,545 B2 * | 7/2021 | Perry ............. C08L 33/08 |
| 2003/0100666 A1 | 5/2003 | Degroot et al. |
| 2005/0106203 A1 | 5/2005 | Roorda et al. |
| 2005/0281866 A1 | 12/2005 | Jarrett et al. |
| 2006/0030669 A1 | 2/2006 | Taton et al. |
| 2007/0049712 A1 | 3/2007 | Allen et al. |
| 2009/0155575 A1 | 6/2009 | Dias et al. |
| 2009/0169715 A1 | 7/2009 | Dias et al. |
| 2010/0114042 A1 | 5/2010 | Dias et al. |
| 2012/0052040 A1 | 3/2012 | Hunter et al. |
| 2012/0082713 A1 | 4/2012 | Meyering et al. |
| 2012/0322954 A1 | 12/2012 | Zupancich et al. |
| 2015/0152270 A1 | 6/2015 | Aizenberg et al. |
| 2015/0316061 A1 | 11/2015 | Hinge et al. |

OTHER PUBLICATIONS

Kasemo, B. Biological surface science. Surf. Sci. 500, 656-677 (2002).
Castner, D. G. & Ratner, B. D. Biomedical surface science: Foundations to frontiers. Surface Science 500, (2002).
Klee, D. & Höcker, H. Polymers for Biomedical Applications: Improvement of the Interface Compatibility. Polymer (Guildf). 149, 222 (1999).
Peppas, N. a., Hilt, J. Z., Khademhosseini, A. & Langer, R. Hydrogels in biology and medicine: From molecular principles to bionanotechnology. Adv. Mater. 18, 1345-1360 (2006).
Hoffman, A. S. Hydrogels for biomedical applications. Adv. Drug Deliv. Rev. 54, 3-12 (2002).
Jagur-Grodzinski, J. Polymeric gels and hydrogels for biomedical and pharmaceutical applications. Polym. Adv. Technol. 21, 27-47 (2010).
Keir, N. & Jones, L. Wettability and silicone hydrogel lenses: a review. Eye Contact Lens 39, 100-8 (2013).
Guillon, M. Are silicone hydrogel contact lenses more comfortable than hydrogel contact lenses? Eye Contact Lens 39, 86-92 (2013).
Nicolson, P. C. & Vogt, J. Soft contact lens polymers: an evolution. Biomaterials 22, 3273-83 (2001).
Luensmann, D. & Jones, L. Protein deposition on contact lenses: The past, the present, and the future. Contact Lens Anterior Eye 35, 53-64 (2012).
Tighe, B. J. A Decade of Silicone Hydrogel Development: Surface Properties, Mechanical Properties, and Ocular Compatibility. Eye Contact Lens Science Clin. Pract. 39, 4-12 (2013).
Grant, C. et al. Poly(vinyl alcohol) hydrogel as a biocompatible viscoelastic mimetic for articular cartilage. Biotechnol. Prog. 22, 1400-1406 (2006).
Keller, J. Literature Review: Silicone Applications in Health Care. (2014).

(Continued)

*Primary Examiner* — Patrick D Niland
(74) *Attorney, Agent, or Firm* — Thomas|Horstemeyer, LLP

(57) ABSTRACT

Embodiments of the present disclosure provide for lubricious structures (also referred to simply as "structure"), methods of making lubricious structures, methods of using lubricious structures, and the like.

5 Claims, 16 Drawing Sheets

(56) References Cited

OTHER PUBLICATIONS

Abbasi, F., Mirzadeh, H. & Katbab, A. A. Modification of polysiloxane polymers for biomedical applications: A review. Polym. Int. 50, 1279-1287 (2001).

Chawla, K. et al. A novel low-friction surface for biomedical applications: modification of poly(dimethylsiloxane) (PDMS) with polyethylene glycol(PEG)-DOPA-lysine. J. Biomed. Mater. Res. A 90, 742-749 (2009).

Colas, A. & Curtis, J. in Biomaterials Science: An Introduction to Materials in Medicine (eds. Ratner, B. D., Hoffman, A. S., Schoen, F. & Lemons, J.) 80-86, 697-707 (Elsevier Academic Press, 2004).

Fonn, D. Targeting contact lens induced dryness and discomfort: what properties will make lenses more comfortable. Optom. Vis. Sci. 84, 279-285 (2007).

Ho, S. P., Nakabayashi, N., Iwasaki, Y., Boland, T. & LaBerge, M. Frictional properties of poly(MPC-co-BMA) phospholipid polymer for catheter applications. Biomaterials 24, 5121-5129 (2003).

Beiko, D. T. et al. Urinary Tract Biomaterials. J. Urol. 171, 2438 2444 (2004).

Hong, S. M., Kim, S. H., Kim, and J. H. & Hwang, H. I. Hydrophilic Surface Modification of PDMS Using Atmospheric RF Plasma. J. Phys. Conf. Ser. 34, 656-661 (2006).

Bhattacharya, S., Datta, A., Berg, J.M. & Gangopadhyay, S. Studies on Surface Wettability of Poly ( Dimethyl ) Siloxane ( PDMS ) and Glass Under Oxygen-Plasma. 14, 590-597 (2005).

Zhang, H. & Chiao, M. Anti-fouling coatings of poly(dimethylsiloxane) devices for biological and biomedical applications. J. Med. Biol. Eng. 35, 143-155 (2015).

Xiao, D., Zhang, H. & Wirth, M. Chemical Modification of the Surface of Poly(dimethylsiloxane) by Atom-Transfer Radical Polymerization of Acrylamide. Langmuir 9971-9976 (2002).

Goda, T., Konno, T., Takai, M., Moro, T. & Ishihara, K. Biomimetic phosphorylcholine polymer grafting from polydimethylsiloxane surface using photo-induced polymerization. Biomaterials 27, 5151-5160 (2006).

Zhang, H. et al. Fabrication of robust hydrogel coatings on polydimethylsiloxane substrates using micropillar anchor structures with chemical surface modification. ACS Appl. Mater. Interfaces 6, 9126-9133 (2014).

Rennie, A. C., Dickrell, P. L. & Sawyer, W. G. Friction coefficient of soft contact lenses: measurements and modeling. Tribol. Lett. 18, 499-504 (2005).

Dunn, A. C. et al. Lubricity of surface hydrogel layers. Tribol. Lett. 49, 371-378 (2013).

Pitenis, A. a. et al. Polymer fluctuation lubrication in hydrogel gemini interfaces. Soft Matter 10, 8955-8962 (2014).

Urueña, J. M. et al. Mesh Size Control of Polymer Fluctuation Lubrication Mechanisms in Gemini Hydrogels. Biotribology 1-2, 24-29 (2015).

Cha, C. et al. Tailoring hydrogel adhesion to polydimethylsiloxane substrates using polysaccharide glue. Angew. Chemie—Int. Ed. 52, 6949-6952 (2013).

Xiameter® RTV-4232-T2 Base Translucent and Translucent high strength silicone moldmaking rubber. Available at: https://www.xiameter.com/EN/Products/Pages/ProductDetail.aspx?pid=02707004&lir=X2256. (Accessed: Jan. 7, 2015).

Lee, C. F., Wen, C. J., Lin, C. L. & Chiu, W. Y. Morphology and temperature responsiveness-swelling relationship of poly(N-isopropylamide-chitosan) copolymers and their application to drug release. J. Polym. Sci. Part A Polym. Chem. 42, 3029-3037 (2004).

Alves, N. M. & Mano, J. F. Chitosan derivatives obtained by chemical modifications for biomedical and environmental applications. Int. J. Biol. Macromol. 43, 401-414 (2008).

Thompson, K. L., Armes, S. P., York, D. W. & Burdis, J. a. Synthesis of sterically-stabilized latexes using weil-defined poly(glycerol monomethacrylate) macromonomers Macromolecules 43, 2169-2177 (2010).

Krüger, P., Knes, R. & Friedrich, J. Surface cleaning by plasma-enhanced desorption of contaminants (PEDC). Surf. Coatings Technol. 112, 240-244 (1999).

Zhang, F. et al. Chemical vapor deposition of three aminosilanes on silicon dioxide: Surface characterization, stability, effects of silane concentration, and cyanine dye adsorption. Langmuir 26, 14648-14654 (2010).

Glass, N. R., Tjeung, R., Chan, P., Yeo, L. Y. & Friend, J. R. Organosilane deposition for microfluidic applications. Biomicrofluidics 5, 1-7 (2011).

Bhushan, B., Hansford, D. & Lee, K. K. Surface modification of silicon and polydimethylsiloxane surfaces with vapor-phase-deposited ultrathin fluorosilane films for biomedical nanodevices. J. Vac. Sci. Technol. A Vacuum, Surfaces, Film. 24, 1197 (2006).

Gilles, S. & Jülich, F. Chemical modification of silicon surfaces for the application in soft lithography. Berichte-Forschungszentrum Julich Jul 4249, (2007).

Liu et al., Immobilization of DNA onto Poly(dimethylsiloxane) Surfaces and Application to a Microelectrechemical Enzyme-Amplified DNA Hybridization Assay. Langmuir 5905-5910 (2004).

Sandison, M. E., Cumming, S. a, Kolch, W. & Pitt, A. R. On-chip immunoprecipitation for protein purification. Lab Chip 10, 2805-13 (2010).

Dunn, A. C., Sawyer, W. G. & Angelini, T. E. Gemini Interfaces in Aqueous Lubrication with Hydrogels. Tribol. Lett. 1-8 (2014).

Schmitz, T. L., Action, J. E., Ziegert, J. C. & Sawyer, W. G. The Difficulty of Measuring Low Friction: Uncertainty Analysis for Friction Coefficient Measurements. J Tribol. 127, 673 (2005).

Tobiesen, F. A. & Michielsen, S. Method for grafting poly(acrylic acid) onto nylon 6,6 using amine end groups on nylon surface. J. Polym. Sci. Part A Polym. Chem. 40, 719-728 (2002).

Goonasekera, C. S., Jack, K. S., Cooper-White, J. J. & Grøndahl, L. Attachment of poly(acrylic acid) to 3-aminopropyltriethoxysilane surface-modified hydroxyapatite. J. Mater. Chem. B 1, 5842 (2013).

Wang, Y. et al. Covalent Micropatteming of Poly ( dimethylsiloxane ) by Photografting through a Mask surface modification on poly ( dimethylsiloxane ) ( PDMS ). 77, 7539-7546 (2005).

Zhang, X., Guan, Y. & Zhang, Y. Dynamically bonded layer-by-layer films for self-regulated insulin release. J. Mater. Chem. 22, 16299 (2012).

Kim, D. & Herr, A. E. Protein immobilization techniques for microfluidic assays. Biomicrofluidics 7, 1-47 (2013).

Marschütz, M. K. & Bernkop-Schnürch, A. Thiolated polymers: Self-crosslinking properties of thiolated 450 kDa poly (acrylic acid) and their influence on mucoadhesion. Eur. J. Pharm. Sci. 15, 387-394 (2002).

Lee, Y. et al. Protein-conjugated, glucose-sensitive surface using fluorescent dendrimer porphyrin. J. Mater. Chem. 19, 5643 (2009).

Pawlak, Z., et al., "The relationship between friction and wettability in aqueous environment", Wear, 2011, pp. 1745-1749, vol. 271, Elsevier B.V., doi: 10.1016/j.wear.2010.12.084.

Kato, Koichi, et al., "Polymer surface with graft chains", Progress in Polymer Science, Feb. 2003, pp. 209-259, vol. 28, No. 2.

Pitenis, Angela A., et al., "Lubricity From Polymer Entangled Networks on Hydrogels", Journal of Tribology, 2016, doi: 10.1115/1.4032889.

Menter, Paul, "Acrylamide Polymerization—A Practical Approach", Bio-Rad, pp. 1-8, tech note/bulletin 1156.

Ishige, T. and A. E. Hamielec, Solution Polymerization of Acrylamide to High Conversion, Journal of Applied Polymer Science, 1973, pp. 1479-1506, vol. 17.

Giz, Ahmet, et al., "Kinetics and Mechanisms of Acrylamide Polymerization from Absolute, Online Monitoring of Polymerization Reaction", Macromolecules, 2001, pp. 1180-1191, vol. 34, No. 5, doi: 10.1021/ma000815s.

Pabon, Martial, et al., "Polymerization of acrylamide in solution and inverse emulsion: number molecular weight distribution with chain transfer agent", Polymer, 1999, pp. 3101-3106, vol. 40, Elsevier Science Ltd.

Abdollahi, Zohreh, and Vincent G. Gomes, "Synthesis and Characterization of Polyacrylamide With Controlled Molar Weight", 2006, pp. 1-7.

Kesari, Haneesh, et al., "Role of Surface Roughness in Hysteresis during Adhesive Elastic Contact", Philosophical Magazine Letters, 2010, pp. 891-902, vol. 90, No. 12, NIH Public Access, doi: 10.1080/09500839.2010.521204.

(56) References Cited

OTHER PUBLICATIONS

De Gennes, P.G., "Dynamics of Entangled Polymer Solutions. I. The Rouse Model", Macromolecules, 1976, pp. 587-593, vol. 9, No. 4.

Liu, Yonggang, et al., "Concentration dependence of the longest relaxation times of dilute and semi-dilute polymer solutions", Journal of Rheology, 2009, pp. 1069-1085, vol. 53, No. 5, The Society of Rheology, doi: 10.1122/1.3160734.

Vazquez, Maribel, et al., "Shear-Induced Degradation of Linear Polyacrylamide Solutions during Pre-Electrophoretic Loading", Analytical Chemistry, 2001, pp. 3035-3044, vol. 73, No. 13, doi: 10.1021/ac001294+.

Odell, J. A. and S. J. Haward, "Viscosity enhancement in the flow of hydrolysed poly(acrylamide) saline solutions around spheres: implications for enhanced oil recovery", Rheological Acta, pp. 129-137, vol. 47, doi: 10.1007/S00397-007-0220-9.

Rudy, Alexander, et al., "Lubricous Hydrogel Surface Coatings on Polydimethylsiloxane (PDMS)", Tribology Letters, 2017, pp. 1-11, vol. 65, No. 3, doi: 10.1007/s11249-016-0783-7.

Hayahara, Takuro and Seiji Takao, "Relationship between Polymer Concentration and Molecular Weight in the Viscosity Behavior of Concentrated Solution", Kolloid-Zeitschrift and Zeitschrift fur Polymere, 1967, pp. 106-111, vol. 225, No. 2.

Vinogradov, G. V. and L. V. Titkova, "Critical Concentrations of Polymers in Solutions According to Measurements of the Viscosity and Specific Surface Area of Aerogels Resulting After Sublimation of the Solvent", Rheologica Acta: An International Journal of Rheology, 1968, pp. 297-306, vol. 7, No. 4.

Fukazawa, Kyoko and Kazuhiko Ishihara, "Simple surface treatment using amphiphilic phospholipid polymers to obtain wetting and lubricity on polydimethylsiloxane-based substrates", Colloids and Surfaces B: Biointerfaces, 2012, pp. 70-76, vol. 97, doi: 10.1016/j.colsurfb.2012.04.008.

Zhou, Jinwen, et al., "Recent developments in PDMS surface modification for microfluidic devices", Electrophoresis, pp. 2-16, vol. 31, doi: 10.1002/elps.200900475.

Moulder, John F., et al., "Handbook of X-ray Photoelectron Spectroscopy", ed. Jill Chastain, 1993, pp. 1-261, Perkin-Elmer Corporation, MN, USA.

Smith, Emily Asenath and Wei Chen, "How To Prevent the Loss of Surface Functionality Derived from Aminosilanes", Langmuir, 2008, pp. 12405-12409, vol. 24, No. 21, doi: 10.1021/la802234x.

Colas, Andre, "Silicones: Preparation, Properties and Performance", Dow Corning, 2005, pp. 1-14, Form No. 01-3077-01, USA.

Stojilovic, Nenad, "Why Can't we See Hydrogen in X-ray Photoelectron Spectroscopy?", Journal of Chemical Education, 2012, pp. 1331-1332, vol. 89, ACS Publications, doi: 10.1021/ed300057j.

Larson, B. J., et al., "Long-Term Reduction in Poly(dimethylsiloxane) Surface Hydrophobicity via Cold-Plasma Treatments", Langmuir, 2013, pp. 12990-12996, vol. 29, ACS Publications, doi: 10.1021/la403077q.

Fetters, Lewis J., "Determination of the Intermolecular Entanglement Coupling Spacings in Polyisoprene by Viscosity Measurements", Journal of Research of the National Bureau of Standards—A. Physics and Chemistry, 1965, pp. 33-37, vol. 69A, No. 1.

Phosphate Buffered Saline Product Description. (2017). http://cellgro.com/phosphate-buffered-saline-1x-2.html. (Accessed: Jun. 2, 2017) Retrieved from https://web.archive.org/web/20170608202720/http://cellgro.com/phosphate-buffered-saline-1x-2.html.

International Search Report and Written Opinion for International Application No. PCT/US17/48649 dated Nov. 9, 2017, 14 pages.

\* cited by examiner

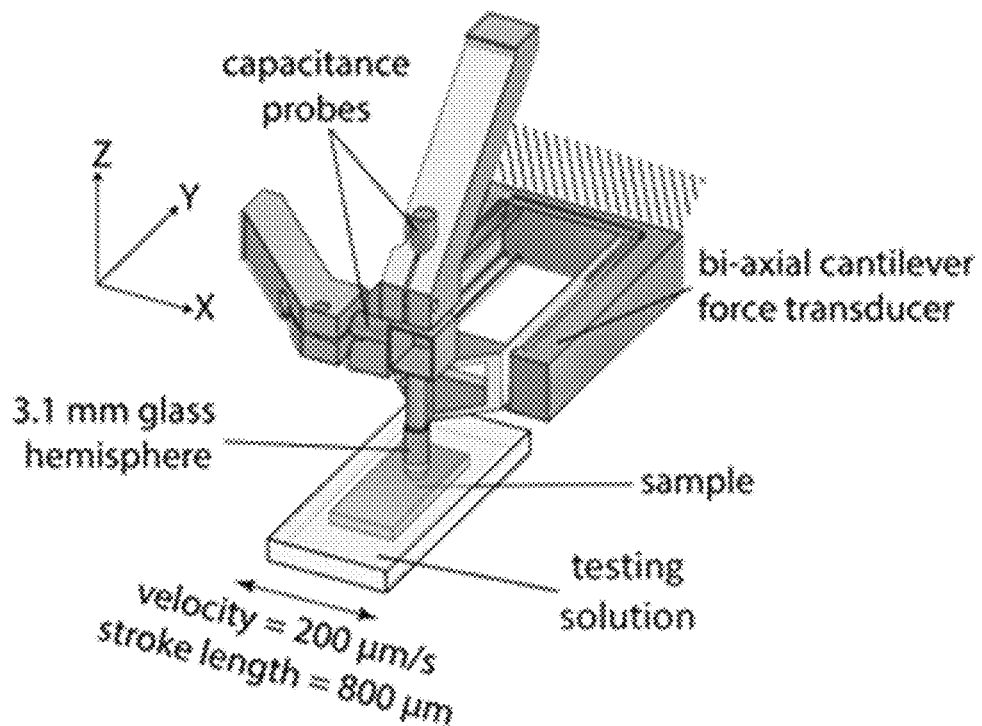
FIG. 1.1
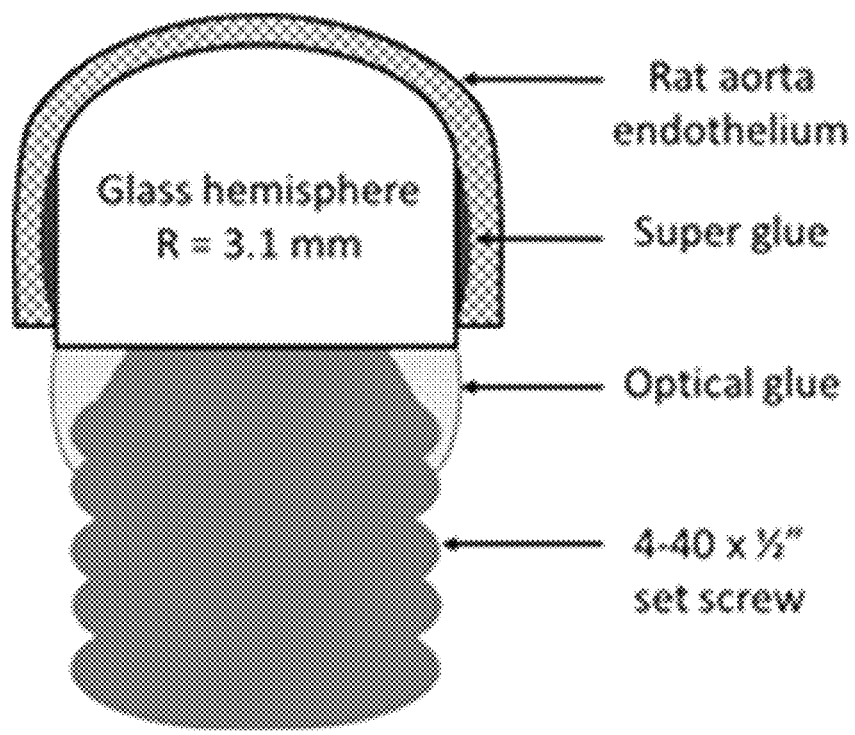
FIG. 1.2

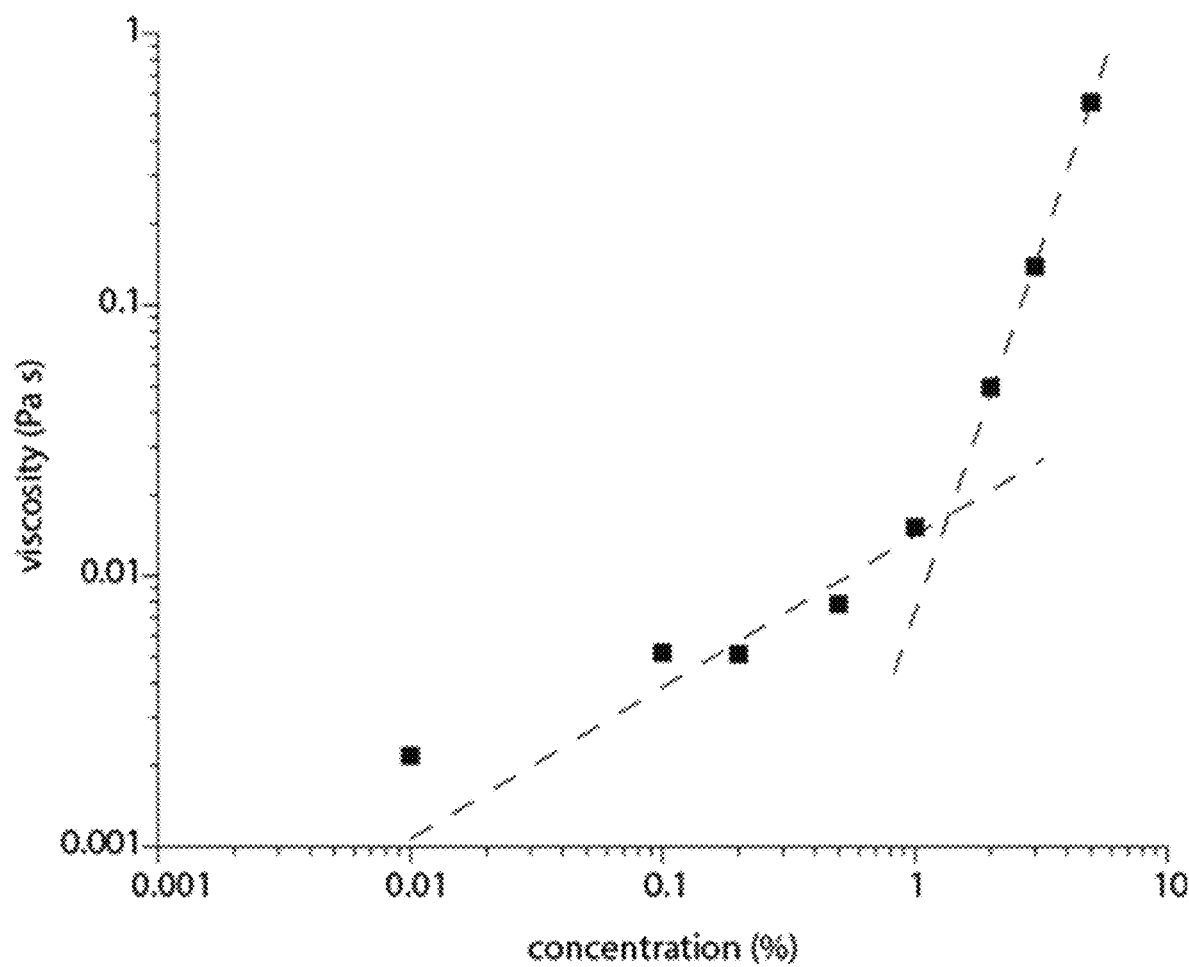
FIG. 1.3

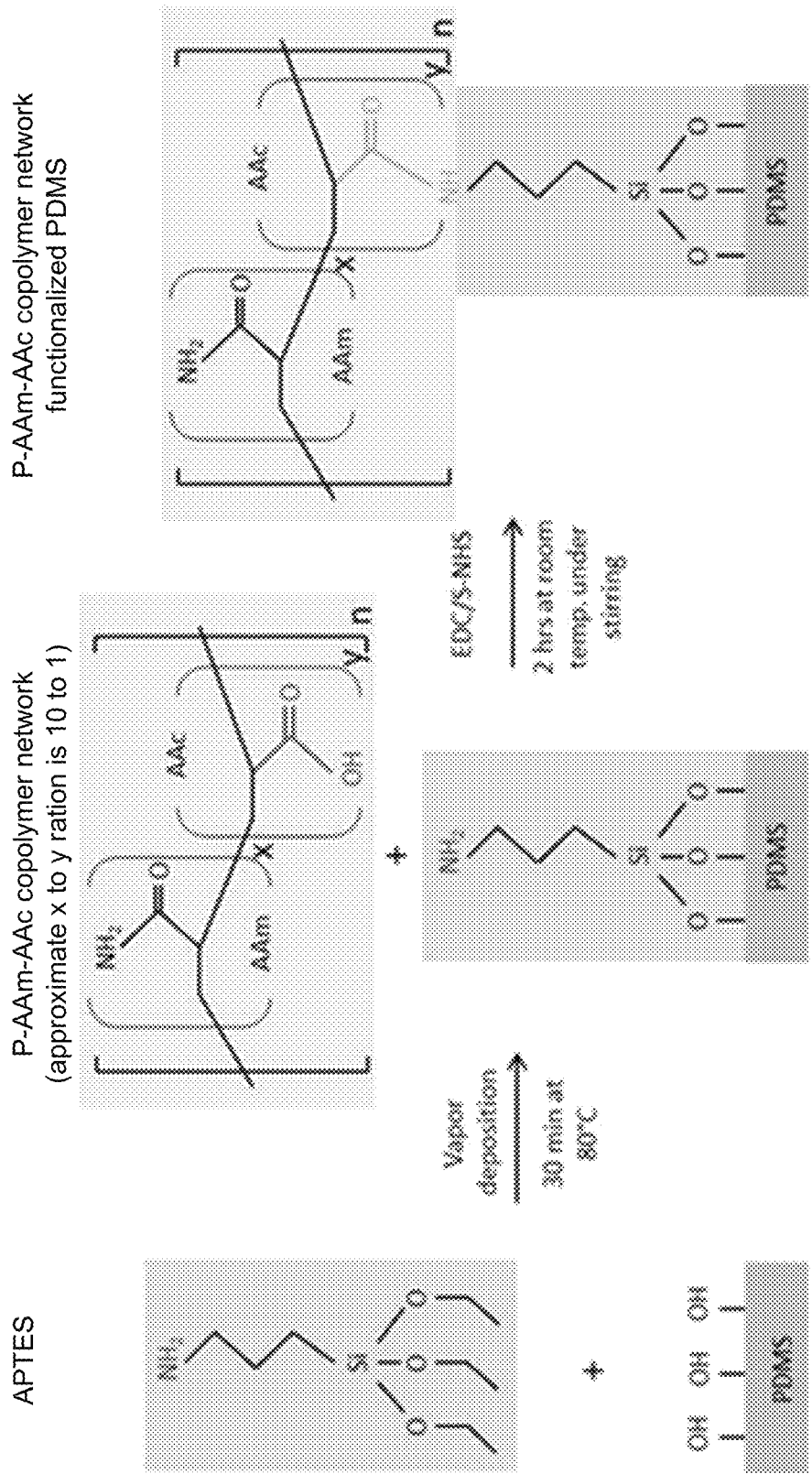
FIG. 1.4

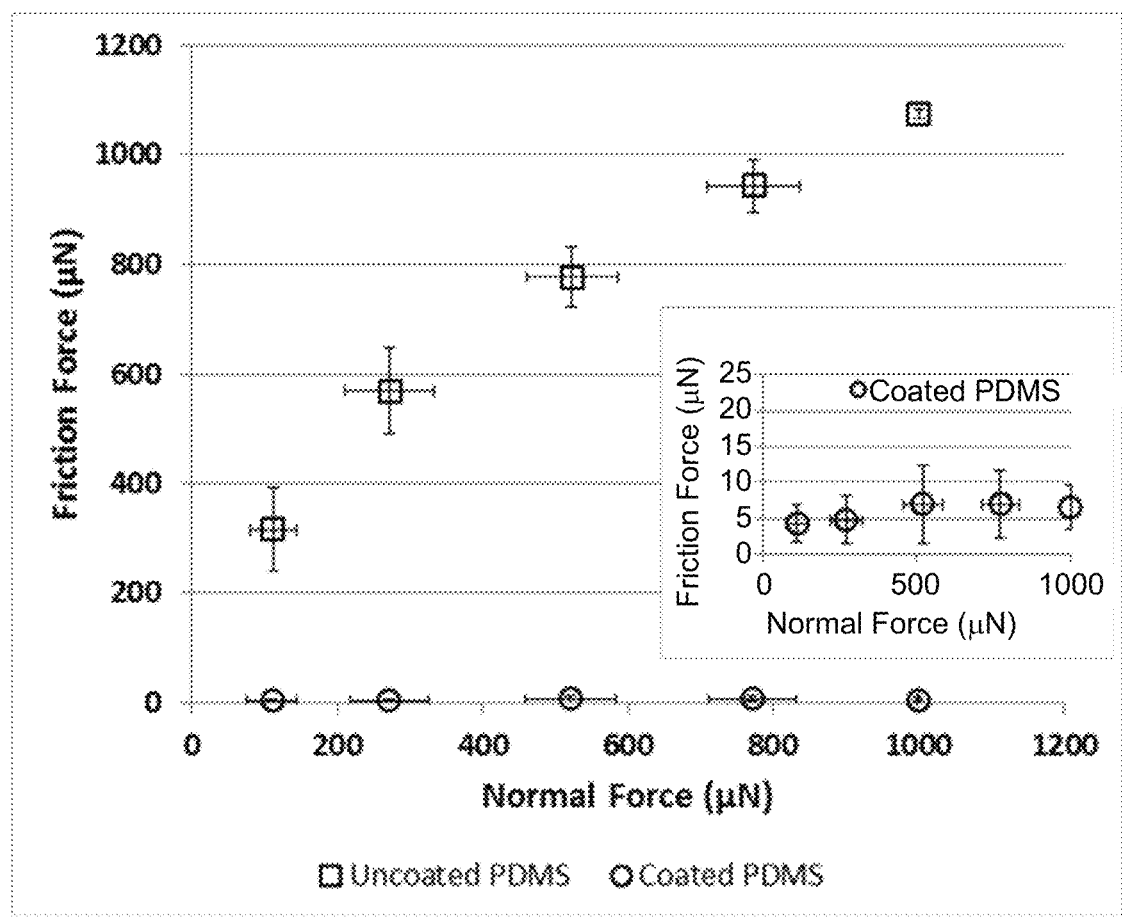
FIG. 1.5

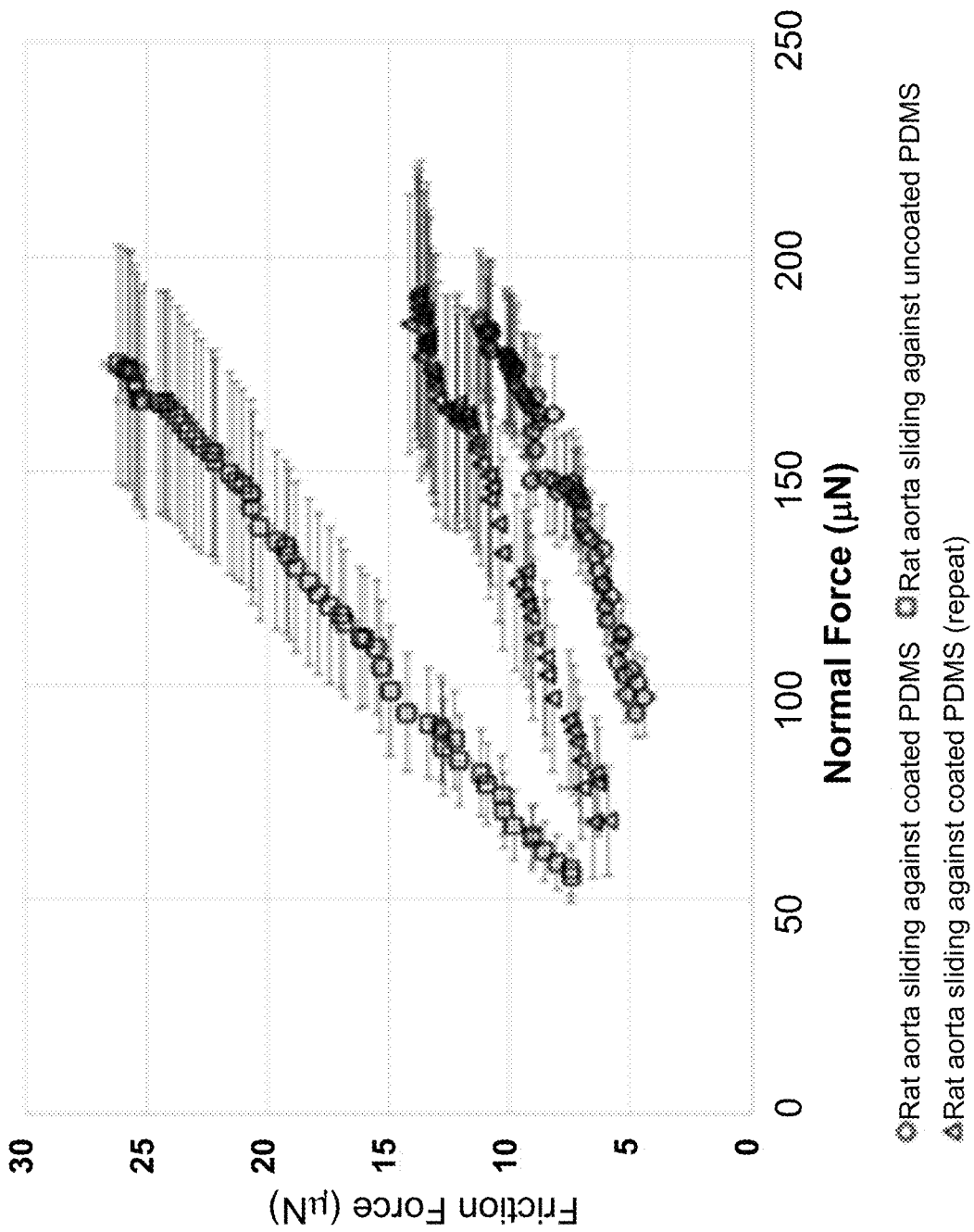
FIG. 1.6

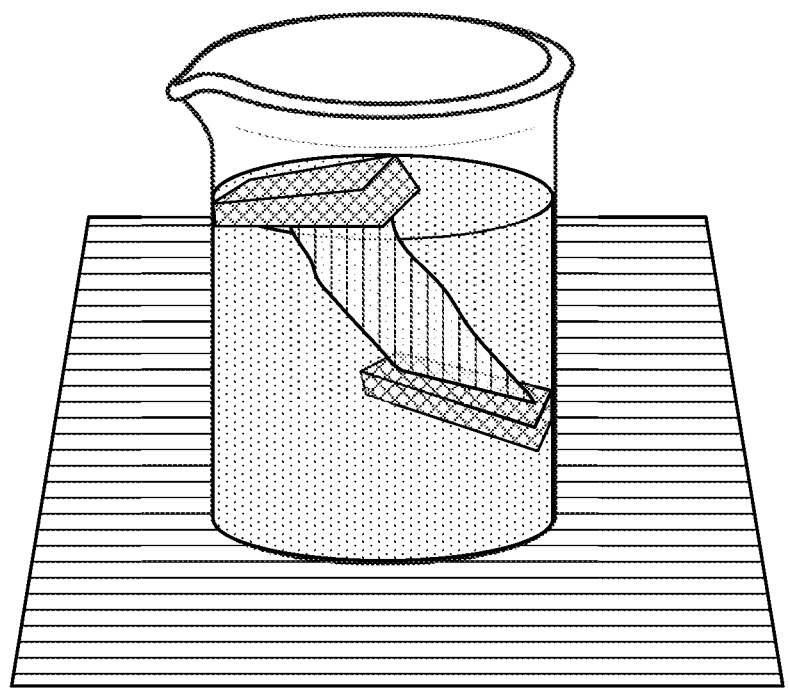
FIG. 2.1
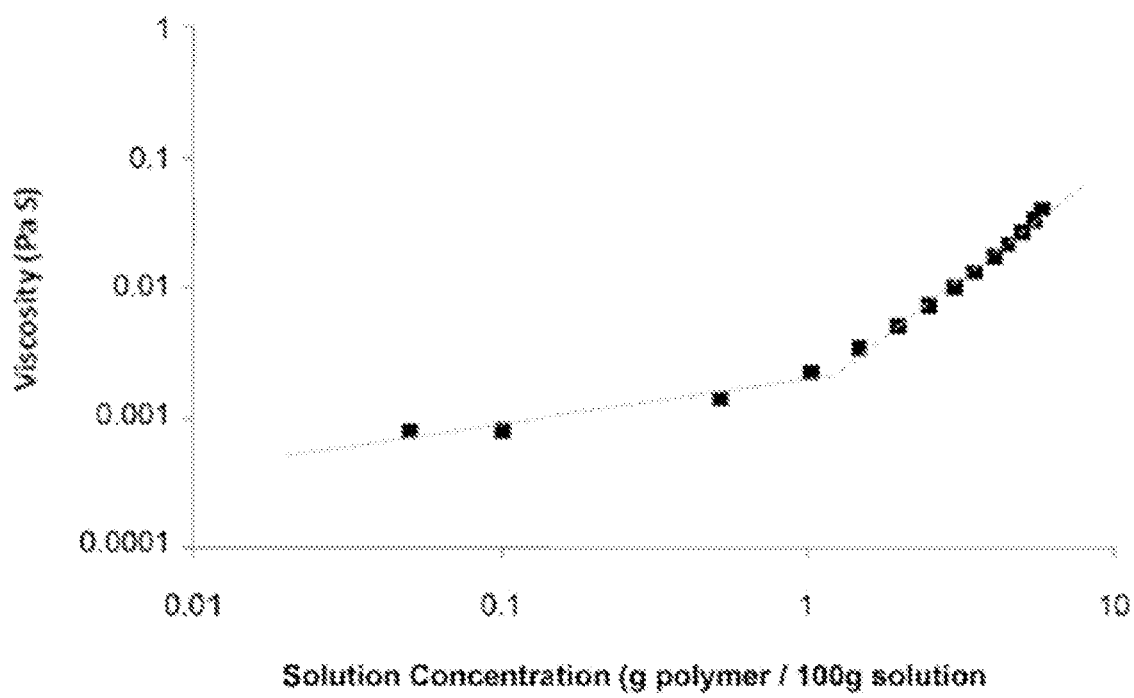
FIG. 2.2

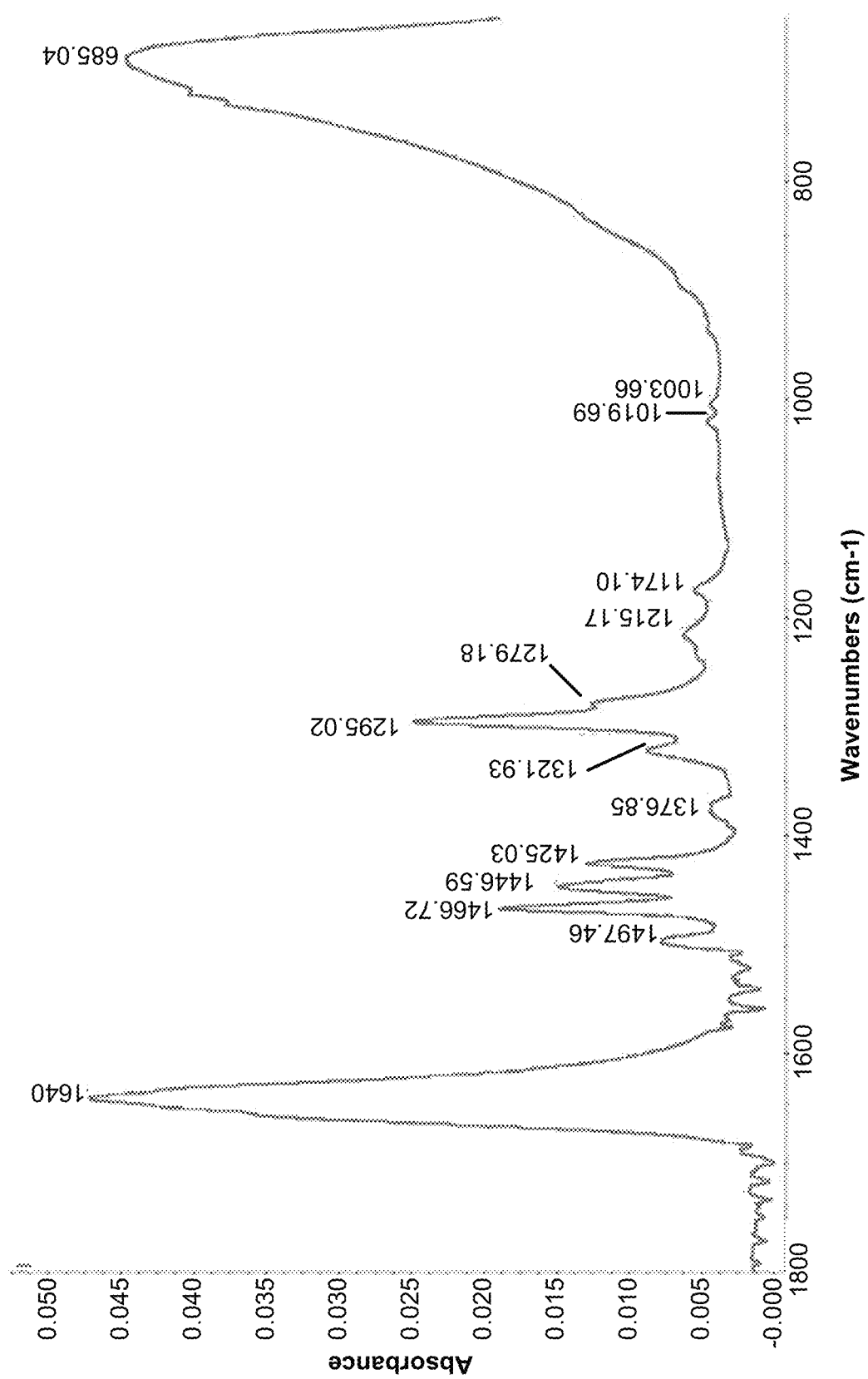
FIG. 2.3

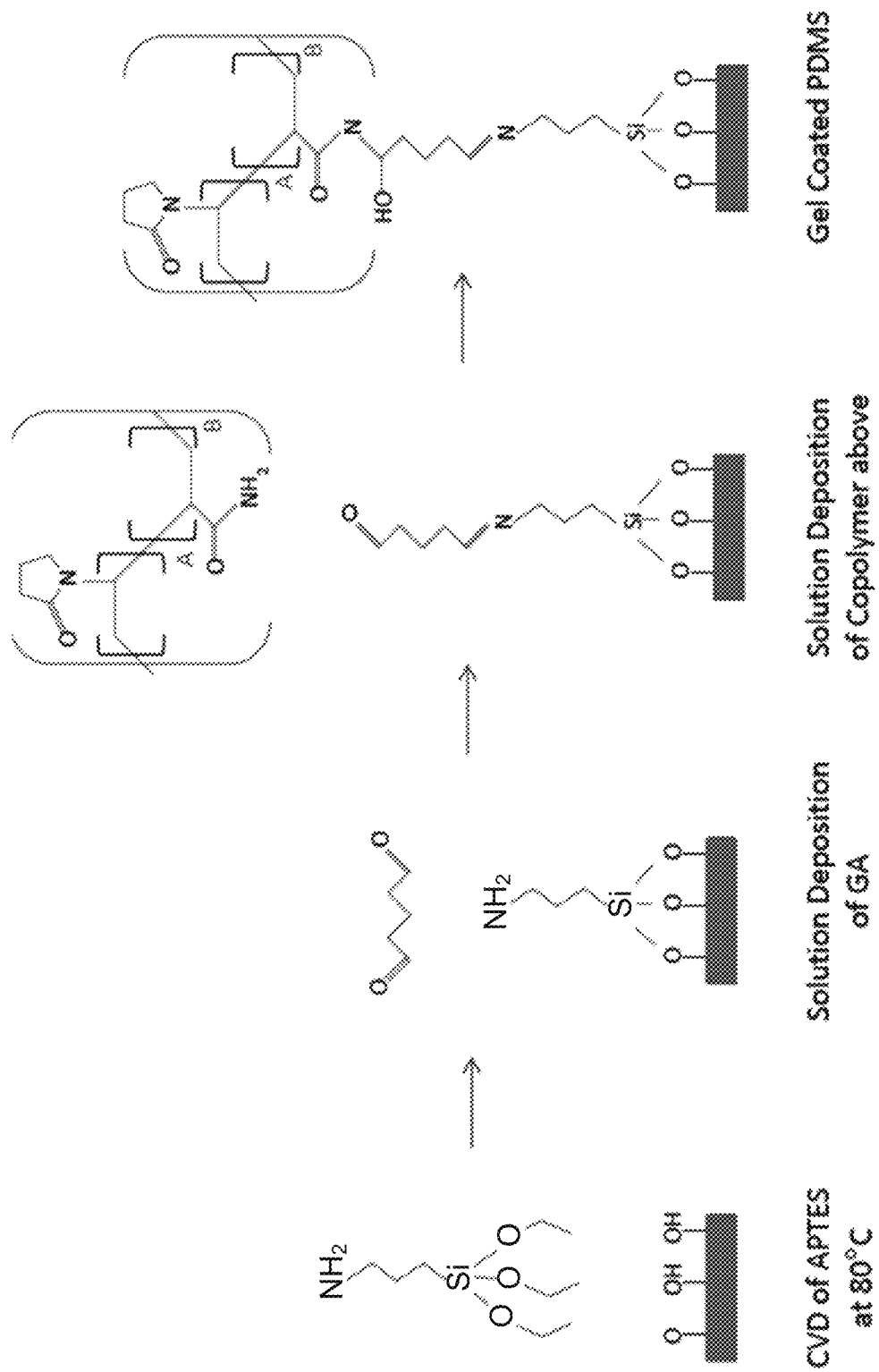
FIG. 3.1

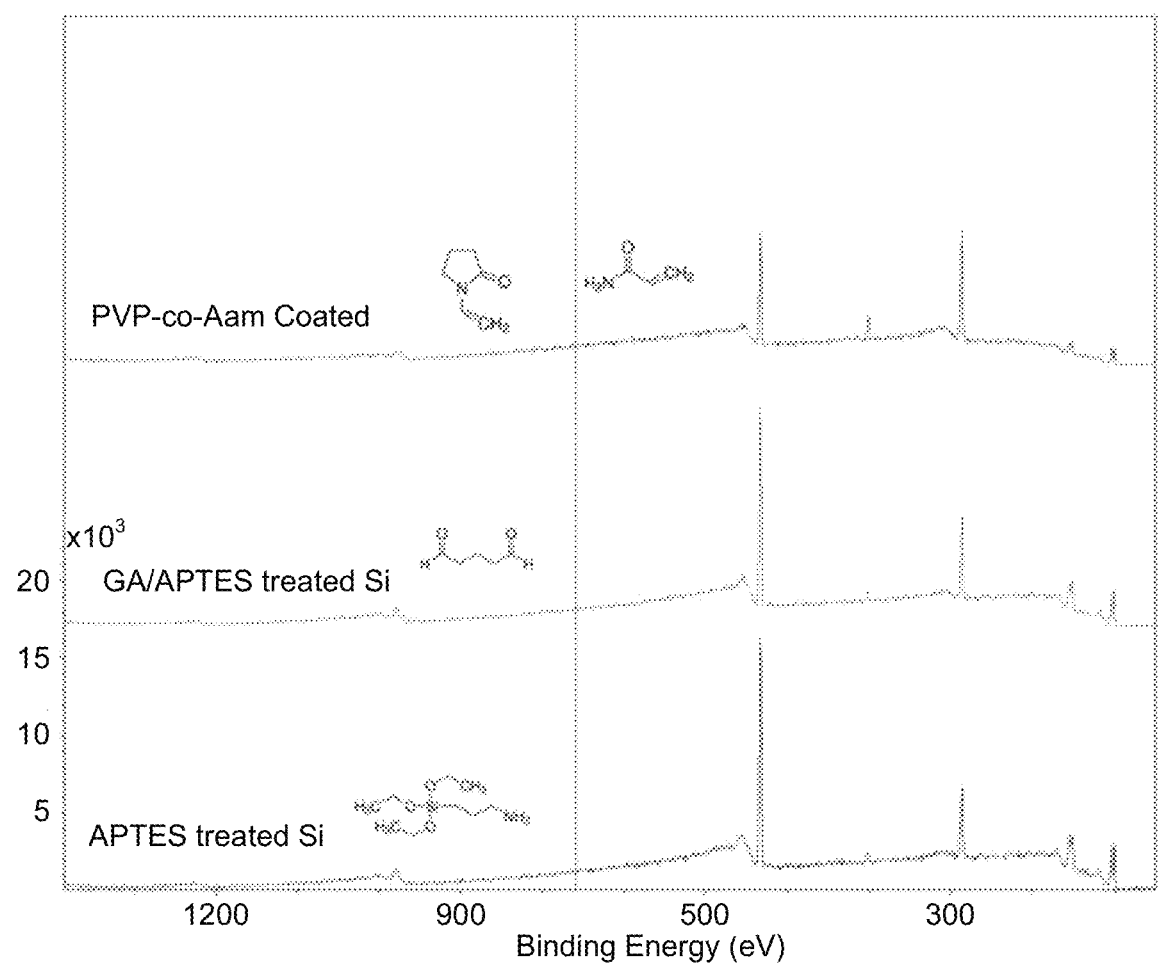
FIG. 3.2

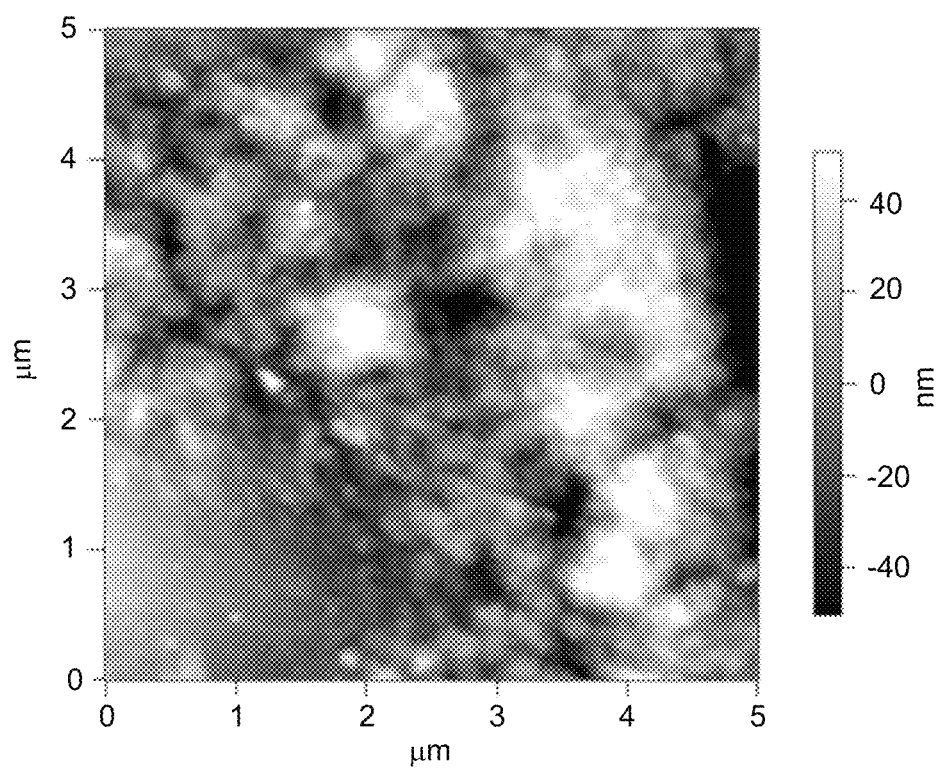
FIG. 3.3
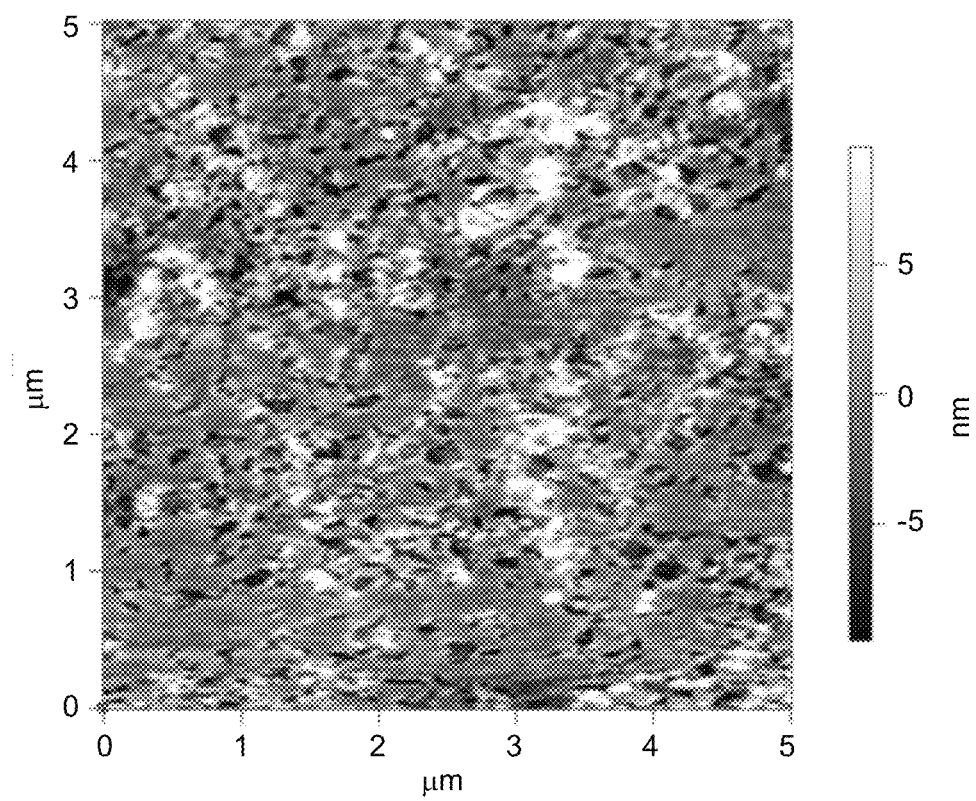
FIG. 3.4

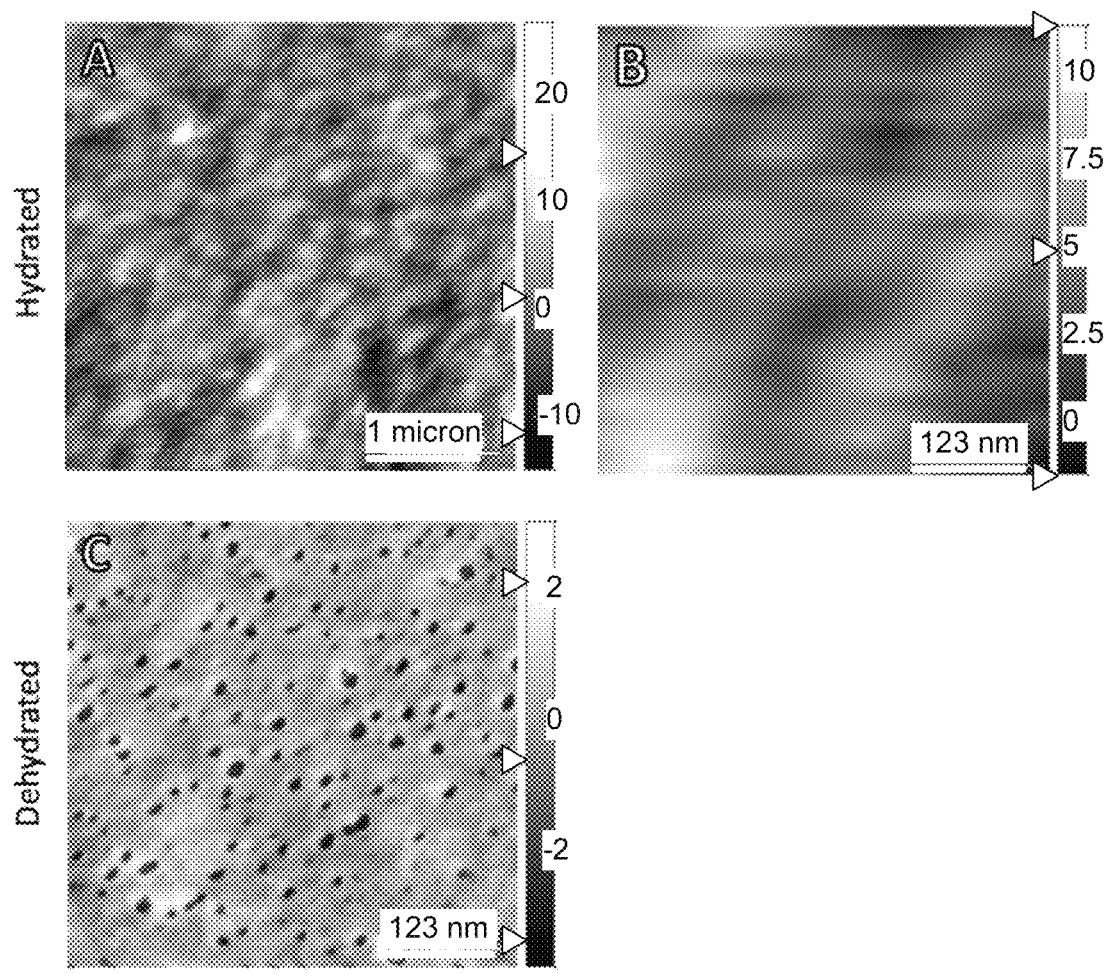
FIG. 3.5

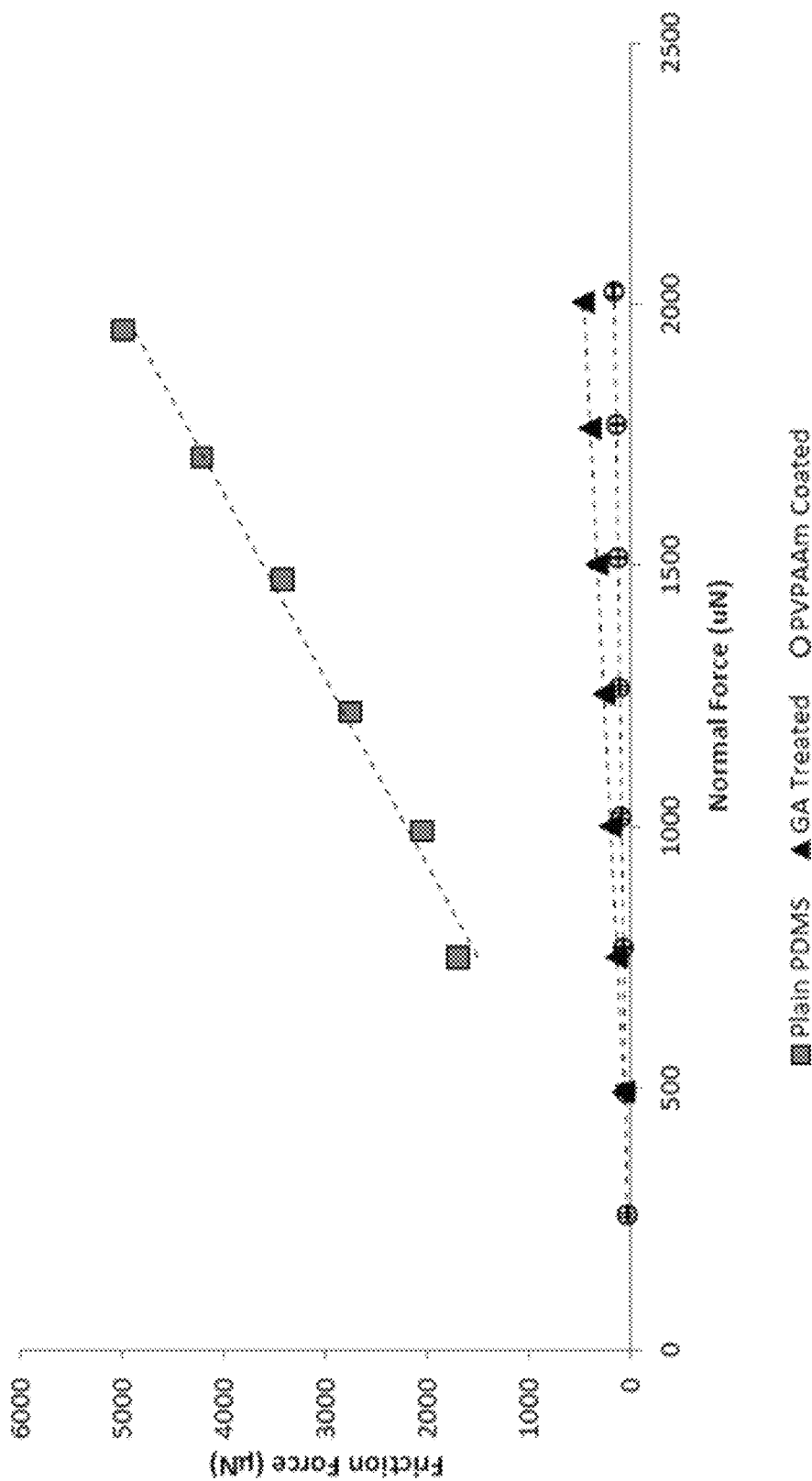
FIG. 3.6

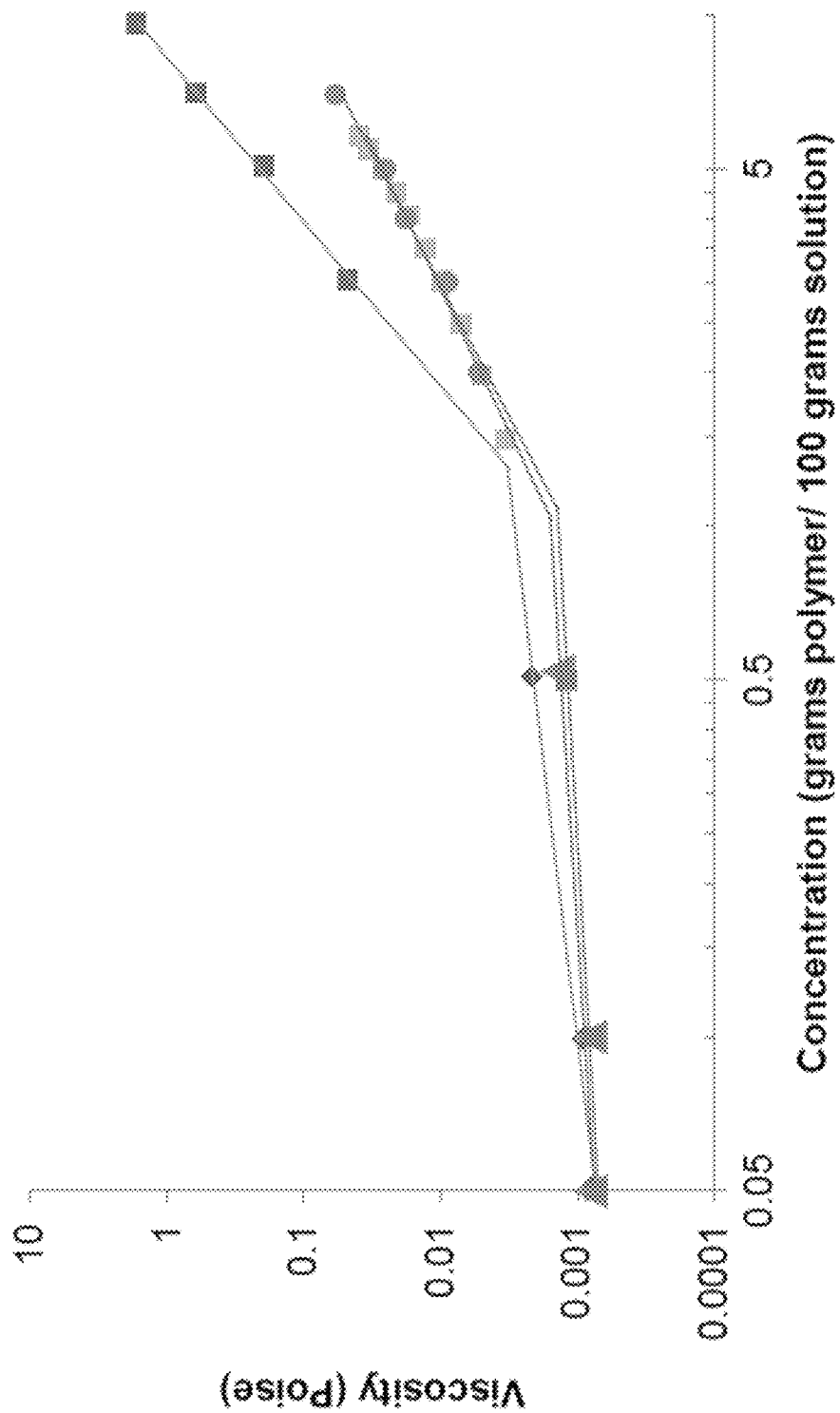
FIG. 4.1

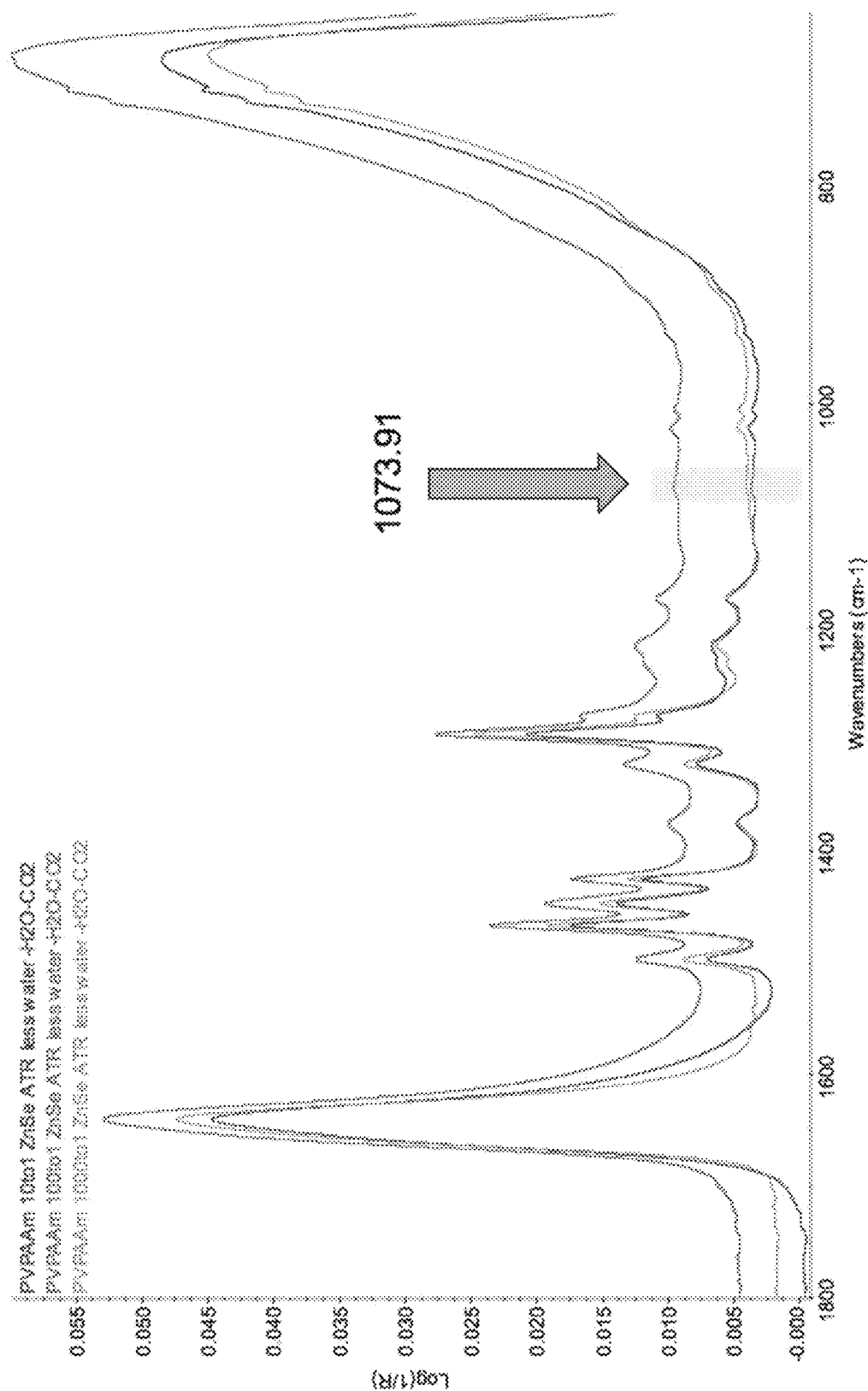
FIG. 4.2

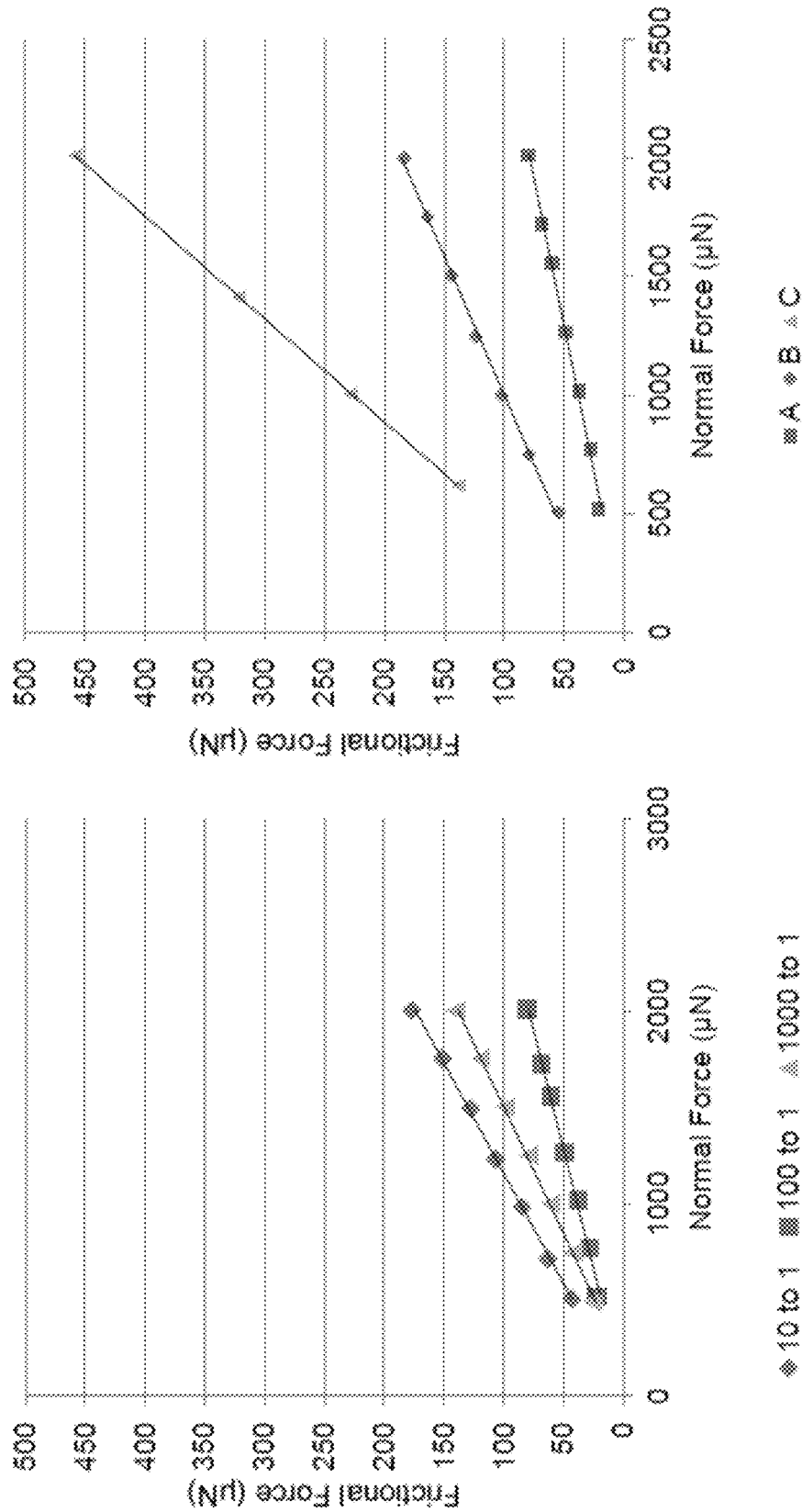
FIG. 4.3

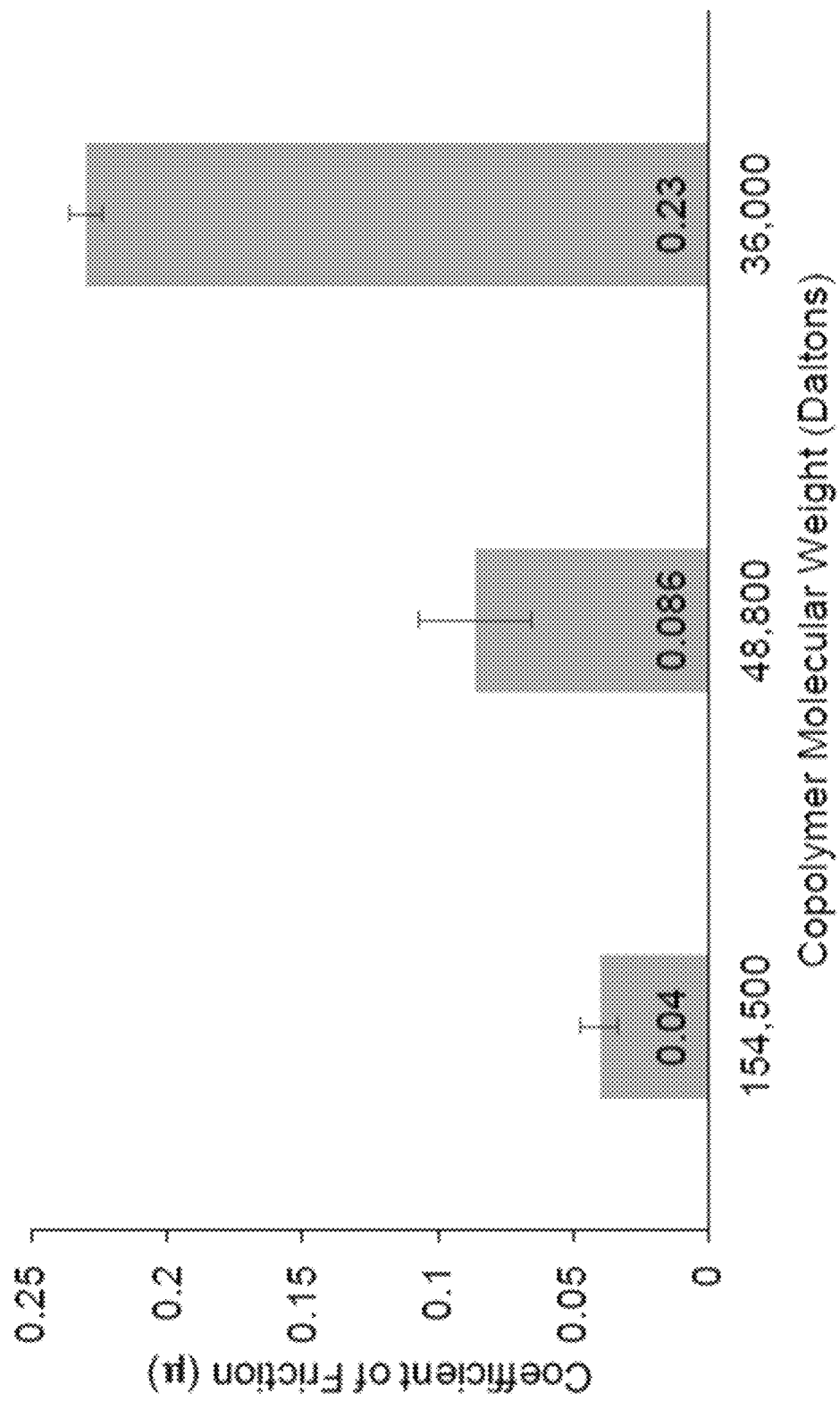
FIG. 4.4

LUBRICIOUS STRUCTURES, METHODS OF MAKING THEM, AND METHODS OF USE

CROSS REFERENCE TO RELATED APPLICATIONS

This application is a continuation of co-pending U.S. patent application Ser. No. 16/327,526, filed on Feb. 22, 2019, entitled "LUBRICIOUS STRUCTURES, METHODS OF MAKING THEM, AND METHODS OF USE," which is the 35 U.S.C. § 371 national stage application of PCT Application No. PCT/US2017/048649, filed Aug. 25, 2017, where the PCT claims priority to, and the benefit of the contents of U.S. provisional application entitled "LUBRICIOUS STRUCTURES, METHODS OF MAKING THEM, AND METHODS OF USE" having Ser. No. 62/379,478, filed Aug. 25, 2016, which is hereby incorporated by reference in its entirety.

BACKGROUND

The study of fundamental interfacial properties has addressed topics of surface energy, material stability, surface modulus, and friction, and hydrogels represent a class of biologically significant materials because their soft, hydrated, fluid permeable polymeric network structures resemble many biological tissues. The introduction of hydrogel coatings represents a promising approach to achieving a high water content, low friction, and biologically inert interface on an otherwise ideal material for applications.

SUMMARY

Embodiments of the present disclosure provide for lubricious structures (also referred to simply as "structure"), methods of making lubricious structures, methods of using lubricious structures, and the like.

One aspect of the disclosure, among others, encompasses a structure, comprising a coating including a physically entangled polymer network, wherein each polymer has a plurality of coupling groups on the main backbone of polymer, and a substrate having a surface, wherein there is a covalent bond between the surface of the substrate and one of the coupling groups. In various aspects, the coating of the structure can include a solvent. In various aspects, the physically entangled polymer network can be a solvated physically entangled polymer network in the solvent, wherein the solvent can be selected from the group consisting of: water, acetone, benzene, n-butyl acetate, carbon tetrachloride, cyclohexane, n-decane, dibutyl amine, dioxane, methanol, ethanol, isopropyl alcohol, ethylene glycol, analine, acetic acid, acetonitrile, ethyl acetate, toluene, and xylene and combination thereof. The physically entangled polymer network of the structure can include a poly(acrylamide-acrylic) random copolymer, wherein the coupling groups, prior to reacting with the substrate surface, of the polymer are acrylic groups. A ratio of acrylamide groups to acrylic groups, prior to reacting with the surface of the substrate, can be about 10:1. The mesh size of the physically entangled network of polymers can be about 5.5 to 8 nm. The substrate can be polydimethylsiloxane (PDMS).

Another aspect of the disclosure, among others, encompasses a method making a lubricious structure, comprising: providing a substrate having a surface; disposing a coating mixture on the surface of the substrate, wherein the coating mixture includes a physically entangled polymer network, wherein each polymer has a plurality of coupling groups on the main backbone of polymer; and forming a coating to the substrate, the coating includes the physically entangled polymer network, wherein there is a covalent bond between the surface of the substrate and one of the plurality of coupling groups. In various aspects, the coating formed in the method includes a solvent. In various aspects, the physically entangled polymer network can be a solvated physically entangled polymer network in the solvent, wherein the solvent is selected from the group consisting of: water, acetone, benzene, n-butyl acetate, carbon tetrachloride, cyclohexane, n-decane, dibutyl amine, dioxane, methanol, ethanol, isopropyl alcohol, ethylene glycol, analine, acetic acid, acetonitrile, ethyl acetate, toluene, and xylene and combination thereof. The physically entangled polymer network can include a poly(acrylamide-acrylic) random copolymer, wherein the coupling groups, prior to reacting with the substrate surface, of the polymer are acrylic groups. A ratio of acrylamide groups to acrylic groups, prior to reacting with the surface of the substrate, can be about 10:1. The physically entangled network of polymers can form a mesh size about 5.5 to 8 nm. The substrate can be polydimethylsiloxane (PDMS).

Another aspect of the disclosure, among others, encompasses a method of making a lubricious structure, comprising: providing a substrate with a surface; synthesizing a physically entangled polymer network; and reacting the physically entangled polymer network with the surface of the substrate to form a coating on the surface of the substrate to form the lubricious structure. In various aspects, synthesizing the physically entangled polymer network comprises free radical polymerization under an inert nitrogen atmosphere. In various aspects, synthesizing the physically entangled polymer network comprises mixing acrylamide groups and acrylic groups, prior to reacting with the surface of the substrate, with a ratio of about 10:1. In various aspects, synthesizing the physically entangled polymer network comprises dialysis in DI H2O. In various aspects, synthesizing the physically entangled polymer network comprises drying the physically entangled polymer network in a vacuum chamber.

Another aspect of the disclosure, among others, encompasses a composition, comprising: a physically entangled polymer network, wherein each polymer has a plurality of coupling groups on the main backbone of polymer. In various aspects, the physically entangled polymer network can be a solvated physically entangled polymer network in a solvent. The physically entangled polymer network can include a poly(acrylamide-acrylic) random copolymer, wherein the coupling groups of the polymer are acrylic groups. A ratio of acrylamide groups to acrylic groups can be about 10:1. The mesh size of the physically entangled network of polymers can be about 5.5 to 8 nm. The solvent can be selected from the group consisting of: water, acetone, benzene, n-butyl acetate, carbon tetrachloride, cyclohexane, n-decane, dibutyl amine, dioxane, methanol, ethanol, isopropyl alcohol, ethylene glycol, analine, acetic acid, acetonitrile, ethyl acetate, toluene, and xylene and combination thereof.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1.1 illustrates an example of a microtribometer experimental setup for friction measurements showing the sample and the probe submerged in testing solution according to various examples described herein.

FIG. 1.2 illustrates an example of a 2-D cross section of the rat aorta probe assembly (not to scale) used for making microtribological friction measurements according to various examples described herein.

FIG. 1.3 illustrates an example of Log-log plot of P-AAm-AAc solution concentration vs. viscosity is indicative of a change in polymer conformation in solution above 1.0 wt % according to various examples described herein.

FIG. 1.4 illustrates an example of a schematic illustrating the methodology for functionalizing hydroxylated PDMS with APTES and P-AAm-AAc copolymer network according to various examples described herein.

FIG. 1.5 illustrates an example of a comparative plot of representative $F_f$ vs. $F_n$ data obtained from friction measurements of uncoated and PDMS samples sliding against a glass probe in PBS according to various examples described herein.

FIG. 1.6 illustrates an example of a comparative plot of $F_f$ vs. $F_n$ data obtained from friction measurements of uncoated and coated PDMS samples slid against a rat aorta probe in PBS according to various examples described herein.

FIG. 2.1 illustrates PVP-co-AAm solution in a dialysis membrane in 1500 ml of DI water according to various examples describe herein.

FIG. 2.2 illustrates a log-log plot of viscosity vs. polymer solution concentration according to various examples describe herein.

FIG. 2.3 illustrates FTIR Spectra of 1000:1 PVP-co-AAm in water according to various examples describe herein.

FIG. 3.1 illustrates an attachment scheme of PVP-co-AAm gel to PDMSe substrate using APTES and GA as linking molecules according to various examples describe herein.

FIG. 3.2 illustrates XPS survey spectra of treatment steps using in attachment of the copolymer to a substrate according to various examples describe herein.

FIG. 3.3 illustrates AFM height image of an untreated PDMSe sample according to various examples describe herein.

FIG. 3.4 illustrates AFM height image of an untreated PDMSe sample according to various examples describe herein.

FIG. 3.5 illustrates tapping mode height AFM images of hydrated (A and B) and dehydrated (C) copolymer coated PDMSe according to various examples describe herein.

FIG. 3.6 illustrates a plot of Friction Force vs Normal Force for untreated PDMSe, GA/APTES treated PDMSe, and PVP-co-AAm coated PDMSe according to various examples describe herein.

FIG. 4.1 illustrates a plot of concentration against viscosity of various monomeric ratio copolymer solutions according to various examples described herein.

FIG. 4.2 illustrates a plot of FTIR spectra of the three various monomeric ratio copolymers according to various examples described herein.

FIG. 4.3 illustrates plots of friction force vs. normal force for all monomeric variation copolymers and all molecular weight variation copolymers according to various examples described herein.

FIG. 4.4 illustrates CoF and standard deviation values for copolymers A, B, and C according to various examples described herein.

DETAILED DESCRIPTION

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, is to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of inorganic chemistry, materials science, nanotechnology and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of inorganic chemistry, materials science, and/or nanotechnology. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

Embodiments of the present disclosure provide for lubricious structures (also referred to simply as "structure"), methods of making lubricious structures, methods of using lubricious structures, and the like. An advantage of the present disclosure includes structures having significantly reduced friction (e.g., two orders of magnitude) compared to currently used technologies. In a particular embodiment, the structures can provide ultra-low friction in aqueous environments and can be used in biologically relevant systems such as catheters, shunts, and microfluidic devices. In addition, embodiments of the present disclosure can be used in other systems such as personal care items (e.g., contact lenses, contraceptives), food packaging, advanced machining, and anti-icing coatings.

In an embodiment, the structure can include a coating on the surface of a substrate. An embodiment of the coating can include a physically entangled polymer network, where the entangled polymers are covalently bonded to the surface of the substrate. In an embodiment, the polymer includes a plurality of coupling groups along the backbone of each polymer, where a covalent bond can be formed between the surface and one or more of the coupling groups. For example, FIG. 1.4 illustrates an embodiment of a reaction scheme to form covalent bonds between acrylic groups on the polymer and (3-aminopropyl)triethoxysilane groups on the surface of the substrate.

In addition, the coating includes a solvent. In an embodiment, the solvent is selected (or paired) so that it supports the physically entangled polymer network through favorable intermolecular interaction. In this regard, the coating is a solvated physically entangled polymer network in a paired solvent. In an embodiment, the physically entangled polymer network can vary in composition. As such, the pairing solvent will vary with composition. The required solvent is selected to be compatible with the physically entangled polymer network such that the Flory Huggins interaction parameter for the polymer-solvent system is less than 0.5. The Flory Huggins parameter describes the interaction energy per solvent molecule per $k_B T$.

In an embodiment, the solvent can include mixtures of molecules; in such cases the relative solvent composition is selected such that the solvents are fully miscible and that there exists a net favorable interaction energy. In an embodiment, the amount of solvent present will be such that the entangled polymer network exists in the semi-dilute regime with a concentration greater than the critical concentration $c^*$. A non-limiting list of solvents that can be used in the present disclosure include: water, acetone, benzene, n-butyl acetate, carbon tetrachloride, cyclohexane, n-decane, dibutyl amine, dioxane, methanol, ethanol, isopropyl alcohol, ethylene glycol, analine, acetic acid, acetonitrile, ethyl acetate, toluene, and xylene and combination thereof.

In general and as used herein, the physically entangled polymer network is formed when high molecular weight polymers exist in either a melt state or at high concentrations such that surrounding chains physically restrict transverse motion of a polymer molecule and that chains are physically intertwined, further defining structure and restricting motion. The points of entanglement, although often treated theoretically as chemical crosslinks, are not permanent and represent only points of physical interaction as opposed to chemical crosslinking. In other words, the physically entangled polymer network is not a chemically (bonded) crosslinked polymer system. The physically entangled polymer network is made up of physically interacting chains and the resulting mesh structure define the physically entangled polymer network.

In an embodiment, the mesh structure includes a network of polymer molecules arranged through physical entanglement such that systematic spaces (voids) exist (mesh size) within the material between/among the polymer molecular chains; such spaces and voids are in turn filled with solvent molecules (e.g., solvent). In an embodiment, the mesh size can be described as the correlation length between all pairs of molecules comprising the polymer network, and in the case of semi-dilute materials made from flexible polymers is of the same order of magnitude as the average spacing between the physical entanglement points.

In an embodiment, the mesh size will depend on the size of the monomers (a, Kuhn length) and the number of monomer units found in the polymer (N). Under this construct, mesh sizes $<(a\ N^{1/2})/10$ define entangled polymer networks. In an embodiment where the physically entangled polymer network is a poly(acrylamide-acrylic) random copolymer and the solvent is water, the mesh size of the physically entangled network of polymers is about 5.5 to 8 nm. Additional details are provided in the Examples.

In an embodiment, the physically entangled polymer network will have a molecular weight (Mw) sufficient to produce entanglement at the working concentration. The limit is set such that the working concentration exceeds the critical concentration $c^*$. In an embodiment, when the physically entangled polymer network includes a poly(acrylamide-acrylic) random copolymer, the weight average molecular weight of 600 kDa corresponds to concentrations greater than 0.007 g/mL.

In an embodiment, the physical entanglement can be determined by measuring the viscosity of the polymer in the solvent as a function of concentration of the polymer. A marked change in the scaling behavior (log scale) of the viscosity as a function of concentration can be observed, and at concentrations above that point, the polymer is considered a physically entangled polymer network. For example, the point at which the marked change occurs is about 1 weight % of poly(acrylamide-acrylic) random copolymer, so that the poly(acrylamide-acrylic) random copolymer is a physically entangled polymer network above this concentration. Additional details are provided in the Example.

As described above, the physically entangled polymer network includes a plurality of polymers. Each polymer has a main polymer backbone and within the backbone is interspersed coupling groups that are used to bond with the surface of the substrate. In an embodiment, the main polymer backbone should possess a linear, flexible molecular structure without side chains or cross links. In addition, the main polymer backbone will have a high molecular weight such that entanglement will occur at the desired working concentration. The main polymer backbone can form a polymer network under semi-dilute conditions through entanglement. Furthermore, the main polymer backbone is compatible with copolymerization schemes needed for addition of coupling groups and bonding of the coupling groups with the surface of the substrate. In an embodiment, the main polymer backbone will have a composition such that it exhibits a linear backbone structure and a pathway to entanglement as well as compatibility with copolymerization with anchor moieties.

In an embodiment, the main polymer backbone can be selected from: polyacrylamide, poly (vinyl alcohol), polyacrylonitrile, polymethacrylonitrile, polyurethanes, polycarbonates, poly(ethylene oxide), poly(propylene oxide), polybutylene oxide, poly(ethylene sulfide), poly(methyl methacrylate), poly(butyl acrylate), poly(butyl methacrylate), poly (vinyl ethyl ether), poly(vinyl butyl ether) poly (vinyl acetate), poly(vinyle chloride)polyethylene, polyisobutylene, co-polymers thereof, and combinations thereof.

In an embodiment, the copolymer monomers that form the coupling groups should be compatible with the synthesis of main polymer (e.g., reaction conditions, phase stability, degree of reactivity). In addition, the coupling group would not substantially alter the solvation properties of main polymer backbone. Furthermore, the coupling group is multifunctional in that the moiety that presents a chemical site to form a thermodynamically stable bond with the main backbone polymer and become part of the main polymer backbone while also forming an irreversible thermodynamically stable chemical bond with substrate. In an embodiment, the coupling group can be selected from: an acrylate, an epoxy, an amine, a mercapto, an isocyanate, a vinyl, an anhydride, a carboxylic acid, a bromine, an imide, or a combination thereof. In general, the ratio of the main backbone polymer to the coupling moiety can be about 10:1 to 1,000:1.

In an embodiment, the physically entangled polymer network includes a poly(acrylamide-acrylic) random copolymer, wherein the coupling groups, prior to reacting with the substrate surface, are the acrylic groups. In an embodiment, the ratio of acrylamide groups to acrylic groups, prior to reacting with the surface of the substrate, can be about 8:1 to 12:1 or about 10:1.

In an embodiment, the substrate can include a wide variety of materials as long as the surface of the substrate can covalently bond with the coupling agent. In this regard, the surface of the substrate is selected (paired) with the coupling agent so that that coupling agent and the surface covalently bond to one another. In an embodiment, the substrate can include glass, ceramic, metals, polymers materials, and covalent solids. In an embodiment, the structure is polydimethylsiloxane (PDMS). In an embodiment, the surface of the substrate can include (e.g., inherently or chemically modified to include) a group having one or more of the following functionalities: an oxide, a hydroxyl, an acrylate, an epoxy, an amine, a mercapto, an isocyanate, a vinyl, an anhydride, a carboxylic acid, a bromine, an imide, or a combination thereof.

As mentioned above, the functionality of the coupling agent can be paired with the appropriate functionality of the surface of the substrate. In one embodiment, the functionality of the surface may be the determining factor for the coupling agent selected whereas in other embodiments the functionality of the coupling agent may be determinative.

In an embodiment in the Example, the substrate is polydimethylsiloxane (PDMS) and the surface has been modified to include a plurality of (amino)silane groups bonded to 0 on the surface of the PDMS, so the acrylic group of the polymer can react with the amino group of the (amino)silane group to form a covalent bond to the substrate.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

Example 1

A surface attached hydrogel made from an entangled network of poly(acrylamide-acrylic) random copolymer chains has been chemically bonded to the surface of polydimethylsiloxane (PDMS) and demonstrated ultra-low friction in aqueous environments. The hydrogel polymer, preformed in solution, possesses a high molecular weight and exists as an entangled network under the solution concentrations employed. Surface attachment is accomplished through chemical modification of the PDMS surface followed by subsequent reaction with acrylic acid moieties along the polymer backbone. The friction coefficients of untreated and hydrogel modified PDMS surfaces were measured via microtribometry, employing both a glass probe and a novel bioprobe made from the anterior surface of a rat thoracic aorta. The unique approach to hydrogel synthesis and its attachment to PDMS succeeds in producing a robust, highly solvated polymer network of sufficient water content to enable friction coefficients as low as $\mu=0.003$.

The study of soft matter interfaces is motivated by their ubiquity in biological systems. With respect to the development of biomaterials, the study of fundamental interfacial properties has addressed topics of surface energy, material stability, surface modulus, and friction [1-3]. Hydrogels represent a class of biologically significant materials because their soft, hydrated, fluid permeable polymeric network structures resemble many biological tissues. In addition, numerous biomedical devices employ hydrogel materials under conditions where these materials interact with biological tissues [4-6]. For example, the modern contact lens represents an application where hydrogels offer, in many instances, low modulus, oxygen permeability, wettability, biocompatibility, and low friction in the ocular environment [7-11]. Numerous other biomaterial applications would benefit from the desirable interfacial properties of hydrogels, but require greater structural strength, toughness, flexibility, and impermeability to drugs and biological agents than afforded by silicone devices [4,12]. To this end, the introduction of hydrogel coatings represents a promising approach to achieving a high water content, low friction, and biologically inert interface on an otherwise ideal material for applications such as catheters and chemotherapy ports.

Polydimethylsiloxane (PDMS) is attractive as a biomaterial due to its ease of fabrication, low modulus, high strain to failure, toughness, high oxygen permeability, impermeability to many drugs, and its relative inertness in aqueous environments [13-16]. In addition, silicone is often the only viable alternative to latex, the use of which is limited in some patients by allergies. After cross-linking, PDMS materials have a hydrophobic surface that is notorious for having unacceptably high friction under aqueous environments against most counter surfaces. In biomedical applications such as urinary catheters and ophthalmic lenses, high interfacial friction has been correlated with discomfort, and tissue damage leading to a general a cascade of negative effects including risk of infection [11,17-19]. Designs and strategies to reduce the friction of PDMS surfaces under aqueous lubrication are being aggressively pursued. Some commonly used techniques include exposing PDMS to an oxygen plasma and corona discharge in order to produce surface silanol groups that increase the surface wettability by water. However, PDMS surfaces rearrange molecularly on the timeframe of minutes and low molecular weight species can migrate to the surface causing the surface to closely resemble its pre-treatment hydrophobic state [14,20-22]. Alternative approaches have explored the introduction of coatings aimed at increasing the hydrophilic nature of PDMS surfaces by grafting polymer chains onto the surfaces [15,23-25]. Due to PDMS's inert surface, activation is required for successful grafting and numerous approaches have been reported including exposure to gamma radiation, surface coronas or plasmas, laser treatments, and incorporation of acrylic monomers during the synthesis. Other approaches to modifying PDMS surfaces have involved the formation of interpenetrating polymeric networks (IPNs), physically mixing PDMS with other polymers, and copolymerization [14,22].

The addition of a chemically bonded, molecularly thick, low friction hydrogel layer to PDMS offers a number of distinct advantages, the foremost being the reduction in friction over the limiting tribological properties of PDMS in aqueous environments. Beyond this, the presence of a hydrogel layer would transform the biomaterial interface with respect to water content and wettability. One of the many attractive properties of PDMS is its resistance to swelling in aqueous environment; the introduction of a hydrogel coating offers the opportunity to have both dimensional stability and toughness with tunable lubricity, controlled through the synthesis of hydrogel. Finally, the addition of a lubricious layer on a soft flexible substrate such as PDMS represents an excellent approach for managing and limiting interfacial contact pressures and the associated interfacial wear and tissue damage that is often associated with the contact of microasperities [26-29]. Similarly, the use of a surface attached hydrogel may reduce contact pressures at delicate tissue surfaces relative to alternative strategies like aqueous polymer brushes, which have contact stiffnesses orders of magnitude higher than those of hydrogels. Two recent studies have reported the introduction of hydrogel layers to PDMS surfaces, by means of either chemical grafting with alginate [30] or physical attachment through the addition of micropillar anchor structures [25], but neither report addressed the impact on interfacial friction.

Herein we report on the chemical attachment of a hydrogel layer composed of a poly(acrylamide-acrylic) random copolymer to PDMS and the subsequent reduction in friction under aqueous environments. The co-polymer, pre-formed in solution, and possesses a high molecular weight. At the conclusion of the polymerization reaction, the solution exists as a thick, mucus like entangled network under the concentrations employed. Surface attachment is accomplished through a multi-step chemical modification of the PDMS surface and the incorporation of acrylic acid moieties along the polymer backbone, thus introducing chemically specific anchor points. Friction has been measured on untreated and hydrogel modified PDMS surfaces via microtribometry, employing both a glass probe and a novel bioprobe made from the anterior surface of a rat thoracic aorta. The unique approach of creating an entangled network in solution followed by attachment to PDMS succeeds in producing a robust, highly solvated polymer network of sufficient mesh size and accompanying water content to enable friction coefficients as low as $\mu=0.003$.

Materials

PDMS was commercially obtained in the form of a base and a curing agent (XIAMETER® RTV-4232-T2 Base Translucent and XIAMETER® T-2 Curing Agent, Dow Corning) and synthesized according to manufacturer's instructions [31]. Hydrochloric acid (HCl, 37% stock solution), (3-aminopropyl)triethoxysilane (APTES, ≥98%), acrylamide (AAm, ≥99%), acrylic acid (AAc, 99%), and 2,2'-azobis(2-methylpropionamidine) dihydrochloride (MBA, 97%) were obtained from Sigma-Aldrich and used as received. 1-ethyl-3-(3-dimethylaminopropyl)carbodiimide hydrochloride (EDC) and N-hydroxysulfosuccinimide (S—NHS) were purchased from Thermo Fisher Scientific and used as received. Phosphate buffered saline (PBS, 1×, pH=7.4, Corning® Cellgro, Mediatech Inc.) was used for synthesis and in tribological measurements.

EXPERIMENTAL

Synthesis of Poly-Acrylamide-Acrylic Acid Copolymer Network

High molecular weight, physically entangled P-AAm-AAc random copolymer networks were synthesized via free radical polymerization under an inert nitrogen atmosphere. AAm and AAc were mixed in a 10 to 1 ratio, respectively, and AIBA was employed as a thermally activated source of free radicals [32-34]. Table 1.1 lists the specific monomer solution composition used to make the P-AAm-AAc copolymer networks examined in this study. Monomer solutions were prepared by mixing all components listed in Table 1.1 in a 50 mL polyethylene (PE) centrifuge tube in a nitrogen filled glove box. The PE tube containing the solution was capped in the glove box. Polymerization was carried out for three hours at 80° C., within the capped PE centrifuge tube.

TABLE 1.1

Monomer solution composition used to prepare P-AAc-AAm copolymer gel.

| Component | Concentration | Amount | Moles | Molarity in Final Solution (M) |
|---|---|---|---|---|
| AAm | 10% solution in DI H2O | 20.0 mL | 0.0281 | 0.703 |
| AAc | 99% | 200.0 µL | $2.92 \times 10^{-3}$ | 0.073 |
| AIBA | 97% | 10.0 mg | $3.69 \times 10^{-5}$ | $9.22 \times 10^{-4}$ |
| DI H2O (deoxygenated) | N/A | 19.8 mL | N/A | N/A |

Following polymerization, the P-AAm-AAc copolymer network underwent dialysis in DI $H_2O$, in order to remove unreacted chemicals and low molecular weight components. To accomplish this, the polymerized network was placed into Spectra/Por® dialysis tubing (volume/cm=9.3 mL, molecular weight cutoff ~3500, dry cylinder diameter=34 mm, dry thickness=0.0013"), submerged in 1000 mL of DI $H_2O$, and dialyzed at room temperature under stirring for three days. During dialysis, the water bath was exchanged twice a day. Following dialysis, the P-AAm-AAc copolymer network was dehydrated by means of rotary evaporation over the course of several hours. The copolymer network was further dried overnight in a vacuum chamber equipped with a roughing pump. The dialyzed and dried P-AAm-AAc copolymer network film was stored in a vacuum desiccator until further use.

GPC of purified copolymer was performed using a Wyatt Technologies miniDAWN™ TREOS multi-angle light scattering system, a Water's corporation 2414 refractive index detector, a Water's ultrahydrogel linear column, and a Viscotek A5000 column. Samples were analyzed in 0.1 M $NaNO_3$ water at a flow rate of 0.5 mL/min and concentrations of 0.5 mg/mL. Molecular weight calculations were performed using ASTRA 6.1 software, and analysis was verified using PEO and PEG standards (20 kg/mol<$M_P$<864 kg/mol, PDI<1.1) purchased from Agilent.

Viscosity Characterization

Dried copolymer was used to prepare a 5 wt % aqueous solution in DI $H_2O$ for the purpose of establishing c*, which is the crossover point between the dilute and semi-dilute regime and provides information on the chain length and corresponding mesh size of the network. Subsequent division and dilution of this sample produced solutions ranging in concentration from 0.01 wt % up to the original 5 wt %. The viscosity of these solutions was measured at room temperature using a Kinexus rheometer (Malvern Instruments, Ltd.). Solution viscosities were recorded as the average of 10 measurements, employing a roughened cone and plate configuration at a shear rate of 100 Hz.

Poly(Dimethylsiloxane) Functionalization

Poly(dimethylsiloxane) sheets (PDMS, XIAMETER® RTV-4232-T2 Base Translucent and XIAMETER® T-2 Curing Agent, Dow Corning) were prepared according to manufacturer's instructions [31]. Briefly, the base and the curing agent (10:1 wt/wt) were manually mixed respectively for five minutes and then degassed in a vacuum chamber and held at ~500 mTorr for ten minutes. The mixture was then cast between two polyethylene terephthalate coated glass plates, separated by 1.6 mm spacers, and allowed to cure for twenty-four hours at room temperature.

PDMS circles (~34 mm diameter) were cut out from the sheets, washed consecutively with a 1% Alconox® solution, acetone, ethanol, and deionized water (DI H2O), dried with a jet of air. Plasma cleaning was performed at 400 mTorr for 2 minutes on a high setting (18 W) using a PDC-32G plasma cleaner (Harrick Plasma Inc., Ithaca, N.Y.) in an atmosphere achieved by bubbling oxygen through a 6% hydrogen peroxide solution. Plasma cleaning of PDMS samples was carried out in order to remove organic contaminants and functionalize the surface with silanol groups that are reactive with the APTES silane agent [20,35].

APTES functionalization of PDMS was performed immediately following plasma cleaning via CVD in order to minimize surface rearrangement [36-40]. Plasma cleaned PDMS samples were placed into a 2.4 L Pyrex® glass vacuum desiccator containing 200 μL of APTES (in an open vial) and pumped down to $10^{-2}$ Torr in order to achieve the desired APTES vapor. A syringe line was then used to introduce HCl vapor (37% v/v) for thirty seconds to the desiccator to catalyze the surface reaction [36,39]. Following HCl exposure, the desiccator was sealed and treated at 80° C. for 30 minutes. Unreacted APTES was removed by rinsing samples with ethanol and DI $H_2O$, and dried under a flow of nitrogen. Sessile drop water contact measurements (2 μL) were performed on the samples within ten minutes of surface functionalization to confirm the presence of APTES. Contact angles in the range of 50-70° matched previously reported values [41]. Functionalized PDMS samples were subjected to subsequent modification steps within 10 minutes of being made.

APTES-treated PDMS samples were placed into 15 mm diameter disposable PS petri dishes, one sample per petri dish. Each sample was completely submerged in a mixture consisting of 1 mL of 2% wt./wt. of P-AAm-AAc/PBS and 1 mL of EDC/S-NHS/PBS solution (100 mg of EDC and 20 mg of S—NHS in 1 mL of PBS) and reacted for 2 hours at room temperature under gentle stirring. Stirring was carried out using a Mistral Multi-Mixer® 4600 (Lab-Line Instruments, Inc.). Coated PDMS samples were removed from and rinsed for 2 minutes under flowing DI $H_2O$.

Microtribometer Friction Measurements

Microtribological experiments were performed using a custom built microtribometer described in detail by Dunn et al. and illustrated in FIG. 1.1 [27,42]. Briefly, a borosilicate glass probe (3.1 mm radius of curvature) was slid against neat and treated PDMS samples in PBS. In all cases, the unmodified side of samples were first dried and then adhered to a polystyrene (PS) dish, in turn mounted to a horizontal, linear reciprocating, piezoelectric stage. The PS dish containing the PDMS sample was filled with PBS to completely cover the sample and the hemispherical probe during tribological measurements. The probe was mounted to a dual titanium flexure cantilever with normal and tangential force constants of 85.9 μN/μm and 72.2 μN/μm, respectively. The sample and the probe were submerged in testing solution (i.e. PBS) during friction measurements.

For some experiments, the probe was modified through the attachment of a section of thoracic rat aorta obtained from a freshly sacrificed animal. This section was used within a few hours of removal and was stored on ice in a PE centrifuge tube filled with Dulbecco's Modified Eagle Medium (DMEM) with 5% Fetal Bovine Serum (FBS) buffer until use. The section of aorta was cut along one side (lengthwise) and unfolded. Approximately 6×6 mm sample was cut out from the unfolded aorta section to be used as the probe for friction measurements. The rat aorta sample was adhered to a glass hemisphere (3.1 mm radius of curvature) mounted on the end of a 4-40×½" set screw using Norland Optical Adhesive 68 (Norland Products Inc., Cranbury, N.J.). The 6×6 mm rat aorta sample was positioned onto a glass hemisphere with the aorta endothelium facing out. The sides of the rat aorta sample were adhered to the glass hemisphere using super glue (Gorilla Glue, Inc.). Probe assembly is illustrated in FIG. 1.2. The rat aorta probe was mounted to a dual titanium flexure cantilever with normal and tangential force constants of 160.7 N/m and 74.6 N/m, respectively.

Forces resulting from tribological interactions of the sample and the probe were measured through normal and lateral capacitive displacement sensors mounted normal to and tangential to the cantilever assembly. The probe was lowered into the PBS solution by a coarse positioning vertical micrometer stage. The measured cantilever displacements arising from buoyancy forces, resulting from submerging the probe in PBS, were reinitialized (i.e. zeroed) prior to sliding. A vertical piezoelectric stage controlled the initial approach of the glass probe to the surface of the sample. This stage was also used to apply monotonically increasing normal loads from ~100 μN to 1500 μN, with at least 20 reciprocating cycles between each increase in normal load. The reciprocating stroke length was 800 μm and the sliding velocity was 200 μm/s. Each reciprocating cycle generated a friction force loop consisting of 400 data points. The middle 20% of the friction force loop was analyzed to calculate the average friction force during sliding for each cycle, using Equation 1.1:

$$F_{t,avg} = \frac{F_{t,forward} - F_{t,reverse}}{2} \quad (1.1)$$

where $F_{t,avg}$ is the average friction force, $F_{t,forward}$ is the friction force in the forward sliding direction, and $F_{t,reverse}$ is the friction force in the reverse sliding direction. The average normal load for each cycle was calculated over the middle 20% of the reciprocating loop. The largest source of normal load uncertainty originated from misalignments in the contact geometry. Ten cycles were averaged for each steady state normal force. The friction coefficient was determined by taking the slope of the curve obtained by fitting friction force ($F_f$) vs. normal force ($F_n$) data and their corresponding uncertainties using a Monte Carlo simulation [43]. For each sample, the microtribological response was evaluated at three different locations. The glass probe used for friction measurement was cleaned with a methanol soaked Kimwipe™ prior to making measurements on new samples or a new location on any given sample.

Results

Polymer Characterization

High molecular weight, physically entangled P-AAm-AAc random copolymer networks were synthesized according the procedures described above. GPC analysis revealed a number average molecular weight of 154±15 kDa, a weight average molecular weight of 643±20 kDa, and a polydispersity index of 4.184±0.434, with uncertainties as calculated by the ASTRA software package. The physical state of the polymer in aqueous solutions was further characterized by viscosity measurements as a function of polymer concentration over the range 0.01 wt % to 5.0 wt %. A marked change in the scaling behavior of viscosity as a function of concentration was observed at ~1.0 wt % polymer. Based on these measurements, a c* of 1.0 wt % is assigned to this P-AAm-AAc polymer and all experiments performed at 1.0 wt % and higher are understood to entail an entangled network. Show in FIG. 1.3 is a log-log plot of P-AAm-AAc solution concentration vs. viscosity is indicative of a change in polymer conformation in solution above 1.0 wt %.

Friction Measurements on PDMS Surfaces

High molecular weight physically entangled P-AAm-AAc random copolymer networks were covalently bonded to APTES functionalized PDMS (FIG. 1.4). Following the procedures outlined above, hydroxylated PDMS was first functionalized with APTES via chemical vapor deposition (CVD) in order to introduce reactive amine functionalities on the surface [36-40]. Subsequently, APTES-treated PDMS was modified through the covalent attachment of P-AAm-AAc via EDC/S—NHS covalent coupling of primary amine and carboxylic acid groups [44-50].

The tribological impact of hydrogel attachment was assessed by measuring the friction coefficient of uncoated and coated PDMS samples, before and after a 12-hour heat treatment in DI $H_2O$ at 80° C. In this set of measurements, sliding occurred in contact with a glass probe immersed in PBS solutions. The uncoated sample was stored for several days in air prior to tribological measurements. Following synthesis, P-AAm-AAc coated samples were vortexed for 15 minutes in DI $H_2O$ to remove any unattached P-AAm-AAc copolymer chains and then stored in 10 mL of fresh DI $H_2O$. The results are presented in FIG. 1.5 and summarized in Table 1.2.

Shown in FIG. 1.5 is a comparative plot of representative $F_f$ vs. $F_n$ data obtained from friction measurements of uncoated (□, μ=0.817±0.050) and coated (○, μ=0.003±0.003) PDMS samples sliding against a glass probe in PBS. Each data point on the friction vs. load plot is an average of 10 friction cycles performed at a given load.

Under the aforementioned testing conditions, uncoated PDMS samples exhibited a significantly higher friction response than the coated PDMS samples. The average friction coefficient of the uncoated PDMS sample was μ=0.887±0.057 while the average of the coated PDMS samples was μ=0.003±0.005. The measured friction coefficient values for coated PDMS samples approached the detection limit of the instrumental setup, which in this configuration is approximately μ=0.002. In order to evaluate the stability of the covalently attached hydrogel network, coated samples were re-measured following and extended exposure to elevated temperatures. Although a slight increase in the COF was observed following heat treatment (Table 1.2), the frictional response remained orders of magnitude lower than that of the PDMS substrate.

TABLE 1.2

Average friction coefficient for sliding contact between a glass probe and uncoated, silanized, and coated PDMS samples in PBS.

| Sample type | Friction Coefficient ± 1 standard deviation |
| --- | --- |
| Uncoated PDMS | μ = 0.887 ± 0.057 |
| Coated PDMS (vortexed) | μ = 0.003 ± 0.005 |
| Coated PDMS (heat treated) | μ = 0.008 ± 0.003 |

A further exploration of the tribological properties of the hydrogel coating entailed friction measurements as a function of solvent quality. To accomplish this, seven sets of friction loops were measured over the range of 0-50 volume % ethanol concentrations (in 18.2 M-ohm water). Instead of measuring friction as a function of load as before, here load was maintained at a constant 500 μN while collecting 10 friction loops over a travel distance of 800 um travel at a sliding speed of 200 μm/s, reporting an average friction coefficient of each experiment set. The friction coefficient doubled upon the introduction of 5% ethanol and continued to increase, approaching μ=0.3, with decreasing solvent quality, which is consistent with the collapse of the surface gel in the poor solvent.

Hydrogel-Tissue Interactions

A probe modified through the attachment of a section of freshly harvested thoracic rat aorta was used to model potential in-vivo interfaces experienced by PDMS based catheter surfaces. The aim here was to evaluate whether the presence of P-AAm-AAc copolymer network on the surface of PDMS produces improvements in interfacial lubricity for contact with a surface composed of endothelium cells common to the linings of arteries. The PDMS samples were prepared according to aforementioned procedures. The tribological evaluation was conducted using a single rat aorta probe, first interrogating the coated PDMS sample, then uncoated PDMS, and then finally the coated sample again. In these measurements, low loads were used in an attempt to prevent damaging the biological tissue of the probe; loads ranged between 50 and 200 μN. Average normal load and friction force data were determined as described above and the friction coefficient was calculated from the slope of the linear fit of $F_f$ VS. $F_n$ plots.

A comparative plot of $F_f$ vs. $F_n$ data obtained from friction measurements of uncoated and coated PDMS samples slid against a rat aorta probe in PBS are represented in FIG. 1.6. Coated sample (○) was measured first, followed by measurements of uncoated PDMS (□), and then a repeat measurement on the coated sample (Δ).

While the COF of the uncoated PDMS sample in contact with the rat aorta endothelium (μ=0.15) is, not surprisingly, lower than that measured with the glass probe, it remains categorically high for an interface entailing an endothelium surface under aqueous conditions. In contrast, measurements of the coated PDMS sample exhibited a low friction (μ=0.07) reflecting the lubricious character of hydrogel coating. Subsequent measurements demonstrated that the friction properties of the hydrogel-coated PDMS sample were independent of the order in which the samples were measured.

DISCUSSION

The synthesis approach described in this work demonstrates a dramatic improvement in the tribological properties of PDMS through functionalization with a surface bound P-AAm-AAc copolymer network. According to the literature, high MW linear PAAm (MW on the order of $10^6$ g/mol) can be formed via aqueous solutions polymerization when the initiator concentration is kept low relative to the monomer concentration and the polymerization reaction is carried out in a deoxygenated environment [51-55]. Similar conditions have been employed here in an effort to produce in solution molecular chains of sufficient length that entanglement will occur under workable polymer concentrations. The results of the GPC characterization demonstrate molecular weights on the order of $10^5$ g/mol; the sizable spread in the molecular weight distribution confirms as well the presence of chains exceeding $10^6$ g/mol.

The synthesis approach aimed at producing high MW linear PAAm chains was augmented specifically to allow the introduction of chemical anchor points along the polymer chain, which is an important strategy as attaching to the end group of the polymer chain is nearly impossible. This was accomplished through the inclusion of acrylic acid (AAc) monomers along the backbone, which are in turn incorporated randomly into the polymer chain through the reaction of the vinyl group. With appropriate functionalization of the PDMS surface, this approach succeeds in (i) producing a specific polymer structure (entangled hydrogel network) in solution and (ii) providing a chemically specific pathway for attachment that does not depend upon endgroup chemistry (FIG. 1.4).

The resulting P-AAm-AAc copolymer network is strongly bound to the PDMS surface. This conclusion is drawn from the observation that coated PDMS samples consistently exhibited low friction responses following vigorous washing with DI $H_2O$ (15 minutes of vortexing), storage of the samples in DI $H_2O$, and heat treatments. Vortexing of samples in DI $H_2O$ was implemented to mechanically remove loosely bound P-AAm-AAc copolymer networks before sample storage in DI $H_2O$. In addition, coated samples were subjected to a 12 hour 80° C. heat treatment in DI $H_2O$ intended to drive potential diffusion and gel disentanglement, thereby evaluating the stability of the coatings. A slight increase in the friction coefficient of coated PDMS following heat treatment was observed; however, the retained low friction coefficient ($\mu$=0.008) demonstrates the successful retention of the copolymer network on the surface. Hydrolysis of APTES-PDMS bonds or of APTES-PDMS bonds represents a mechanism for detachment for changes in the surface bound P-AAm-AAc copolymer network layer. Given that the friction and wetting properties of the silanized PDMS samples before and after analogous heat treatments were very similar, the hydrolysis of the APTES likely does not affect the stability of coatings [36]. The P-AAm-AAc copolymer treated PDMS samples consistently exhibited low friction throughout the evaluations, demonstrating that the coatings are robust, strongly bound to the surface, and highly lubricious.

From the microtribological results, it is clear that the presence of P-AAm-AAc copolymer network on the surface of PDMS significantly reduced interfacial friction between the PDMS sample surface and the glass probe under aqueous conditions. Interactions between the glass probe and uncoated PDMS resulted in very high CoF, in contrast to the coated PDMS, which exhibited an extremely low CoF in sliding contact with the glass probe. From an interfacial perspective, an additional difference entails the dramatic increase in hydrophilicity. Upon attachment of the hydrogel layer, both DI $H_2O$ and PBS completely wet the PDMS surface. The favorable interactions with water introduced through the presence of the hydrogel are in turn seen to reduce adhesion between glass and PDMS [58,59] as well as to modify the fundamental nature of frictional interactions at the interface. Given the measured friction coefficient of $\mu$=0.003, it is concluded that the presence of the P-AAm-AAc copolymer network on the surface of PDMS reduces the friction forces with the glass probe by altering the interface contact mechanics and introducing the requisite structure associated with the regime of fluctuation lubrication [28].

Previous studies of linear (non-crosslinked) PAAm networks revealed that the mesh size ($\xi$, in angstroms) of these networks follows the relationship $$\xi = 2.09 C^{-0.76 \pm 0.03} \tag{1.1}$$

when the concentration (C) is greater than the critical concentration for entanglements (c*), which represents the concentration where polymer chains begin to interact with each other and the solution transitions into the semi-dilute regime [61,62]. It is possible to estimate c using the following equation.

$$c^* = \frac{3M}{4\pi N_A R_g^3} \tag{1.2}$$

Here M is the molar mass, $N_A$ is the Avogadro number, and $R_g$ is the radius of gyration, which can be approximated by $$R_g \sim b N^\nu \tag{1.3}$$

In this expression, b is the monomer size (0.154 nm for C—C bond), N is the number of Kuhn monomers (equal to DP), and $\nu$ is the excluded volume scaling exponent (equal to 0.5 in a $\theta$ solvent and 0.588 in a good solvent) [60]. Table 1.2 provides a theoretical estimate of c* for PAAm with MW in the range of $10^5$ to $10^6$ g/mol. As can be seen, PAAm solutions entailing polymer chains in this MW range enter into the semi-dilute regime between 3 and 0.5 wt %, respectively. The GPC and viscosity results presented above correlate well with this estimate. The results empirically establish that the P-AAm-AAc solutions employed here, consisting of a distribution of molecular weight chains, exhibit a c* of ~1 wt %. Correspondingly, Equation 1.1 can be applied to determine $\xi$ when C>c*. During attachment of the entangled P-AAm-AAc hydrogel to PDMS, C=2% and the mesh size $\xi$ is estimate to be 6 to 7.9 nm.

TABLE 1.3

Theoretical values of DP, MW, $R_g$, and c* for PAAm in a good solvent.

| DP | MW (g/mol) | $R_g$ (nm) | c* (g/mL) |
|---|---|---|---|
| 1407 | 100009.56 | 10.932 | 0.030 |
| 14069 | 1000024.52 | 42.335 | 0.005 |

Note that in Table 1.3, DP values were chosen to be whole numbers that yield MW values closest to $10^5$ and $10^6$ g/mol. End groups were not considered in the analysis. MW was obtained by multiplying the DP by molar mass of AAm (71.08 g/mol). $R_g$ and c* were calculated using Equations 1.3 and 1.2, respectively, which yield values comparable to those reported in the literature [53,61,62].

It is this structural feature, namely the large mesh size associated with the entangled P-AAm-AAc network that gives rise to the favorable interfacial properties observed. First, the introduction of a highly solvated hydrogel network to the PDMS surface is seen to modify the contact mechanics by providing a low modulus surface [28,29]. This in turn is seen to significantly reduce local contact pressures at the interface. Second, the large mesh size and correlated low polymer density for the P-AAm-AAc network is seen to produce a unique structure at the sliding interface. Recent work has clearly demonstrated that hydrogel friction can be described in terms of polymer fluctuation under the sliding speeds employed here. The large mesh sizes associated with the entangled network attached to the PDMS surface result in a greatly reduced friction coefficient.

Hydrogel properties in the past have typically been explored using hard, impermeable probes. These test conditions differ from those found within the biological environment, where interactions occur between soft, permeable materials. Recent micro-tribometer hydrogel friction studies have reported that the friction behavior between a hard probe and a hydrogel substrate can differ significantly from that of a soft hydrogel probe and the identical hydrogel substrate. The emerging understanding is that in order to better simulate behavior under biological conditions using hydrogels, soft hydrogel probes should be used for measurements of hydrogel substrates [28,42]. As the P-AAm-AAc copolymer network coatings for PDMS hold potential significance in terms of biological applications, friction measurements were repeated using a tissue section of a rat thoracic aorta ax the contacting probe surface. The results (FIG. 1.6) demonstrate that the low friction measured on the P-AAm-AAc modified PDMS persists when sliding against biologic tissue in PBS. Although the friction is higher than when measured with a glass probe, it is likely due to issues of surface roughness and the complex composition of the cell and extracellular matrix surface. Nonetheless, the results clearly demonstrate the potential of such an approach for reducing friction at PDMS surfaces in applications where friction and the corresponding tissue damage, such as in catheters [11,17-19], is a primary concern. In this study friction tests were performed in PBS at room temperature. Additional testing is needed under conditions more closely matching the biological environment to more fully evaluate the performance of these coatings in vivo.

CONCLUSIONS

The chemical attachment of a hydrogel layer composed of a poly(acrylamide-acrylic) random copolymer to a PDMS surface served to reduce friction, measured in contact with a glass probe under aqueous conditions, by more than two orders of magnitude. The hydrogel, preformed in solution, exists as an entangled network is covalently bound to functionalized PDMS through acrylic acid moieties along the polymer backbone. This approach to chemically anchoring the hydrogel layer, preserves, at the surface, the mesh size of the entangled network formed in solution. The creation of this highly hydrated hydrogel structure introduces the novel mechanism of thermal fluctuation lubrication to the surface of the typically-high-friction PDMS. The reduction in friction is seen to persist when the coated PDMS surface is placed in contact with tissue samples consisting of endothelium cells, highlighting potential pathways to reducing friction at the interfaces of biomedical devices composed of PDMS.

References, Example 1

1. Kasemo, B. Biological surface science. *Surf. Sci.* 500, 656-677 (2002).
2. Castner, D. G. & Ratner, B. D. Biomedical surface science: Foundations to frontiers. *Surface Science* 500, (2002).
3. Klee, D. & Wicker, H. Polymers for Biomedical Applications: Improvement of the Interface Compatibility. *Polymer (Guildfi.* 149, 222 (1999).
4. Peppas, N. a., Hilt, J. Z., Khademhosseini, A. & Langer, R. Hydrogels in biology and medicine: From molecular principles to bionanotechnology. *Adv. Mater.* 18, 1345-1360 (2006).
5. Hoffman, A. S. Hydrogels for biomedical applications. *Adv. Drug Deliv. Rev.* 54, 3-12 (2002).
6. Jagur-Grodzinski, J. Polymeric gels and hydrogels for biomedical and pharmaceutical applications. *Polym. Adv. Technol.* 21, 27-47 (2010).
7. Keir, N. & Jones, L. Wettability and silicone hydrogel lenses: a review. *Eye Contact Lens* 39, 100-8 (2013).
8. Guillon, M. Are silicone hydrogel contact lenses more comfortable than hydrogel contact lenses? *Eye Contact Lens* 39, 86-92 (2013).
9. Nicolson, P. C. & Vogt, J. Soft contact lens polymers: an evolution. *Biomaterials* 22, 3273-83 (2001).
10. Luensmann, D. & Jones, L. Protein deposition on contact lenses: The past, the present, and the future. *Contact Lens Anterior Eye* 35, 53-64 (2012).
11. Tighe, B. J. A Decade of Silicone Hydrogel Development: Surface Properties, Mechanical Properties, and Ocular Compatibility. *Eye Contact Lens-Science Clin. Pract.* 39, 4-12 (2013).
12. Grant, C. et al. Poly(vinyl alcohol) hydrogel as a biocompatible viscoelastic mimetic for articular cartilage. *Biotechnol. Prog.* 22, 1400-1406 (2006).
13. Keller, J. Literature Review: Silicone Applications in Health Care. (2014).
14. Abbasi, F., Mirzadeh, H. & Katbab, A. A. Modification of polysiloxane polymers for biomedical applications: A review. *Polym. Int.* 50, 1279-1287 (2001).
15. Chawla, K. et al. A novel low-friction surface for biomedical applications: modification of poly(dimethylsiloxane) (PDMS) with polyethylene glycol(PEG)-DOPA-lysine. *J. Biomed. Mater. Res. A* 90, 742-749 (2009).
16. Colas, A. & Curtis, J. in *Biomaterials Science: An Introduction to Materials in Medicine* (eds. Ratner, B. D., Hoffman, A. S., Schoen, F. & Lemons, J.) 80-86, 697-707 (Elsevier Academic Press, 2004).
17. Fonn, D. Targeting contact lens induced dryness and discomfort: what properties will make lenses more comfortable. *Optom. Vis. Sci.* 84, 279-285 (2007).
18. Ho, S. P., Nakabayashi, N., Iwasaki, Y., Boland, T. & LaBerge, M. Frictional properties of poly(MPC-co-BMA) phospholipid polymer for catheter applications. *Biomaterials* 24, 5121-5129 (2003).
19. BEIKO, D. T. et al. Urinary Tract Biomaterials. *J. Urol.* 171, 2438-2444 (2004).
20. Hong, S. M., Kim, S. H., Kim, and J. H. & Hwang, H. I. Hydrophilic Surface Modification of PDMS Using Atmospheric RF Plasma. *J. Phys. Conf. Ser.* 34, 656-661 (2006).
21. Rie, A. Studies on Surface Wettability of Poly (Dimethyl) Siloxane (PDMS) and Glass Under Oxygen-Plasma. 14, 590-597 (2005).

22. Zhang, H. & Chiao, M. Anti-fouling coatings of poly (dimethylsiloxane) devices for biological and biomedical applications. *J. Med. Biol. Eng.* 35, 143-155 (2015).
23. Xiao, D., Zhang, H. & Wirth, M. Chemical Modification of the Surface of Poly(dimethylsiloxane) by Atom-Transfer Radical Polymerization of Acrylamide. *Langmuir* 9971-9976 (2002).
24. Goda, T., Konno, T., Takai, M., Moro, T. & Ishihara, K. Biomimetic phosphorylcholine polymer grafting from polydimethylsiloxane surface using photo-induced polymerization. *Biomaterials* 27, 5151-5160 (2006).
25. Zhang, H. et al. Fabrication of robust hydrogel coatings on polydimethylsiloxane substrates using micropillar anchor structures with chemical surface modification. *ACS Appl. Mater. Interfaces* 6, 9126-9133 (2014).
26. Rennie, A. C., Dickrell, P. L. & Sawyer, W. G. Friction coefficient of soft contact lenses: measurements and modeling. *Tribol. Lett.* 18, 499-504 (2005).
27. Dunn, A. C. et al. Lubricity of surface hydrogel layers. *Tribol. Lett.* 49, 371-378 (2013).
28. Pitenis, A. a. et al. Polymer fluctuation lubrication in hydrogel gemini interfaces. *Soft Matter* 10, 8955-8962 (2014).
29. Urueña, J. M. et al. Mesh Size Control of Polymer Fluctuation Lubrication Mechanisms in Gemini Hydrogels. *Biotribology* 1-2, 24-29 (2015).
30. Cha, C. et al. Tailoring hydrogel adhesion to polydimethylsiloxane substrates using polysaccharide glue. *Angew. Chemie—Int. Ed.* 52, 6949-6952 (2013).
31. XIAMETER® RTV-4232-T2 Base Translucent and Translucent high strength silicone moldmaking rubber. Available at: https://www.xiameter.com/EN/Products/Pages/ProductDetail.aspx?pid=02707004&lir=X225 6. (Accessed: 7 Jan. 2015)
32. Lee, C. F., Wen, C. J., Lin, C. L. & Chiu, W. Y. Morphology and temperature responsiveness-swelling relationship of poly(N-isopropylamide-chitosan) copolymers and their application to drug release. *J. Polym. Sci. Part A Polym. Chem.* 42, 3029-3037 (2004).
33. Alves, N. M. & Mano, J. F. Chitosan derivatives obtained by chemical modifications for biomedical and environmental applications. *Int. J. Biol. Macromol.* 43, 401-414 (2008).
34. Thompson, K. L., Armes, S. P., York, D. W. & Burdis, J. a. Synthesis of sterically-stabilized latexes using weildefined poly(glycerol monomethacrylate) macromonomers. *Macromolecules* 43, 2169-2177 (2010).
35. Kruger, P., Knes, R. & Friedrich, J. Surface cleaning by plasma-enhanced desorption of contaminants (PEDC). *Surf. Coatings Technol.* 112, 240-244 (1999).
36. Zhang, F. et al. Chemical vapor deposition of three aminosilanes on silicon dioxide: Surface characterization, stability, effects of silane concentration, and cyanine dye adsorption. *Langmuir* 26, 14648-14654 (2010).
37. Glass, N. R., Tjeung, R., Chan, P., Yeo, L. Y. & Friend, J. R. Organosilane deposition for microfluidic applications. *Biomicrofluidics* 5, 1-7 (2011).
38. Bhushan, B., Hansford, D. & Lee, K. K. Surface modification of silicon and polydimethylsiloxane surfaces with vapor-phase-deposited ultrathin fluorosilane films for biomedical nanodevices. *J. Vac. Sci. Technol. A Vacuum, Surfaces, Film.* 24, 1197 (2006).
39. Gilles, S. & Jülich, F. Chemical modification of silicon surfaces for the application in soft lithography. *Berichte-Forschungszentrum Julich Jul* 4249, (2007).
40. Immobilization of DNA onto Poly(dimethylsiloxane) Surfaces and Application to a Microelectrechemical Enzyme-Amplified DNA Hybridization Assay. *Langmuir* 5905-5910 (2004).
41. Sandison, M. E., Cumming, S. a, Kolch, W. & Pitt, A. R. On-chip immunoprecipitation for protein purification. *Lab Chip* 10, 2805-13 (2010).
42. Dunn, A. C., Sawyer, W. G. & Angelini, T. E. Gemini Interfaces in Aqueous Lubrication with Hydrogels. *Tribol. Lett.* 1-8 (2014). doi:10.1007/s11249-014-0308-1
43. Schmitz, T. L., Action, J. E., Ziegert, J. C. & Sawyer, W. G. The Difficulty of Measuring Low Friction: Uncertainty Analysis for Friction Coefficient Measurements. *J. Tribol.* 127, 673 (2005).
44. Tobiesen, F. A. & Michielsen, S. Method for grafting poly(acrylic acid) onto nylon 6,6 using amine end groups on nylon surface. *J. Polym. Sci. Part A Polym. Chem.* 40, 719-728 (2002).
45. Goonasekera, C. S., Jack, K. S., Cooper-White, J. J. & Grøndahl, L. Attachment of poly(acrylic acid) to 3-aminopropyltriethoxysilane surface-modified hydroxyapatite. *J. Mater. Chem. B* 1, 5842 (2013).
46. Wang, Y. et al. Covalent Micropatterning of Poly (dimethylsiloxane) by Photografting through a Mask surface modification on poly (dimethylsiloxane) (PDMS). 77, 7539-7546 (2005).
47. Zhang, X., Guan, Y. & Zhang, Y. Dynamically bonded layer-by-layer films for self-regulated insulin release. *J. Mater. Chem.* 22, 16299 (2012).
48. Kim, D. & Herr, A. E. Protein immobilization techniques for microfluidic assays. *Biomicrofluidics* 7, 1-47 (2013).
49. Marschütz, M. K. & Bernkop-Schnürch, A. Thiolated polymers: Self-crosslinking properties of thiolated 450 kDa poly(acrylic acid) and their influence on mucoadhesion. *Eur. J. Pharm. Sci.* 15, 387-394 (2002).
50. Lee, Y. et al. Protein-conjugated, glucose-sensitive surface using fluorescent dendrimer porphyrin. *J. Mater. Chem.* 19, 5643 (2009).
51. Menter, P. *Acrylamide Polymerization—A Practical Approach*.
52. Ishige, T. & Hamielec, A. E. Solution Polymerization of Acrylamide to High Conversion. *J. Appl. Polym. Sci.* 17, 1479-1506 (1973).
53. Giz, A., Çatalgil-Giz, H., Alb, A., Brousseau, J.-L. & Reed, W. F. Kinetics and Mechanisms of Acrylamide Polymerization from Absolute, Online Monitoring of Polymerization Reaction. *Macromolecules* 34, 1180-1191 (2001).
54. Pabon, M. & Selb, J. Polymerization of acrylamide in solution and inverse emulsion: number molecular weight distribution with chain transfer agent. 40, 3101-3106 (2006).
55. Abdollahi, Z. & Gomes, V. G. Synthesis and Characterization of Polyacrylamide with Controlled Molar Weight. 1-7 (2006).
56. Kesari, H., Doll, J. C., Pruitt, B. L., Cai, W. & Lew, A. J. Role of Surface Roughness in Hysteresis during Adhesive Elastic Contact. 90, 891-902 (2011).
57. Pawlak, Z., Urbaniak, W. & Oloyede, a. The relationship between friction and wettability in aqueous environment. *Wear* 271, 1745-1749 (2011).
58. De Gennes, P. G. Dynamics of Entangled Polymer Solutions. I. The Rouse Model. *Macromolecules* 9, 587-593 (1976).
59. *Handbook of Capillary and Microchip Electrophoresis and Associated Microtechniques*. (CRC Press, 2008).

60. Liu, Y., Jun, Y. & Steinberg, V. Concentration dependence of the longest relaxation times of dilute and semi-dilute polymer solutions. *J. Rheol.* (N. Y. N. Y). 53, 1069 (2009).
61. Vazquez, M., Schmalzing, D., Matsudaira, P., Ehrlich, D. & McKinley, G.
Shear-Induced Degradation of Linear Polyacrylamide Solutions during Pre-Electrophoretic Loading. *Anal. Chem.* 73, 3035-3044 (2001).
62. Odell, J. a. & Haward, S. J. Viscosity enhancement in the flow of hydrolysed poly(acrylamide) saline solutions around spheres: implications for enhanced oil recovery. *Rheol. Acta* 47, 129-137 (2007).

Example 2

Materials

Acrylamide (AAm, 99%), 1-vinyl-2-pyrrolidone (VP, ≥99%), and 2,2'-azobis(2-methylpropionamidine) dihydrochloride (AIBA, 97%) were obtained from Sigma-Aldrich and used as received. DI water with a maximum 18 mΩ resistivity was generated in house using a Barnstead NanoPure™ Diamond water purification system.

Copolymer Synthesis

High molecular weight, linear, random copolymer chains of poly(vinylpyrrolidone-co-acrylamide) (PVP-co-AAm) were created by free radical polymerization. The molecular formulae of constituents are listed in Table 2.1. Vinyl Pyrrolidone (7.98 ml, $7.38*10^{-3}$ moles), acrylamide (0.0053 g, $0.0747*10^{-3}$ moles), MBA (60 mg, $22.125*10^{-5}$ moles), and DI water (142.02 ml, 7.98 moles) were added to a stoppered flask where nitrogen was bubbled directly into the solution via a needle pierced through the stopper connected to a nitrogen tank. A separate needle was also fed through the stopper to allow air to flow out and to avoid the overpressurization of the system. Nitrogen bubbling was carried out for two hours to remove oxygen from the reaction vessel and solution; oxygen acts as a free radical scavenger and will limit the molecular weight of the final copolymer. The needles were removed and the vessel was submerged in a water bath agitated with a stir bar at 60° C. The polymerization took place undisturbed for 4 hours then was quenched by exposure to air (oxygen in the atmosphere acts as a free radical scavenger and stops any further polymerization that may occur). The resulting copolymer was dialyzed for a minimum of 3 days in at least 1000 ml of deionized water (DI water) while agitated with a stir bar. The water was changed twice daily to ensure that a sufficient diffusion gradient for the dialysis procedure was maintained. Spectra/Por (ID dialysis tubing with a molecular weight cutoff of ~3.5 kDa was used to remove unreacted monomers and low molecular weight components.

TABLE 2.1

Components and concentrations of chemical used in synthesis of the copolymer corresponding to a 1000:1 PVP-co-AAm copolymer

| Component | Amount | Moles | Molarity(M) |
|---|---|---|---|
| Vinyl Pyrrolidone | 7.98 ml | $7.38e^{-3}$ | 0.0492 |
| Acrylamide | 0.0053 g | $0.0747e^{-3}$ | $0.498e^{-3}$ |
| AIBA | 0.060 g | $22.125e^{-5}$ | $1.475e^{-3}$ |
| DI H2O | 142.02 ml | 9.66 | — |

The dialysis setup can be seen in FIG. 2.1 sans the stir bar and plate. Shown is PVP-co-AAm solution in a dialysis membrane in 1500 ml of DI water. The dialysis membrane is clipped at the ends with the white tubing clamps. The actual dialysis took place on a stir plate with a magnetic stir bar agitating the water at all times.

After dialysis, the copolymer was dried by a rotary evaporation until the polymer became a transparent solid. In short, a Rotavapor® R (BUCHI Labortechnik) was employed to evaporate water from dialyzed copolymer. This was achieved by placing the dialyzed copolymer solution into a 500 mL round bottomed flask then pulling vacuum while the flask was rotated in a heated water bath. A set of two condensing traps were used to remove the water vapor, the first of which was ice bath cooled and the second was liquid nitrogen. The polymer was further dehydrated overnight in a vacuum environment of approximately 0.2 Torr. Full removal of water is critical for accurate rheometer measurements. The dehydrated polymer was used to create stock solutions for rheological characterization and copolymer gel deposition via chemical attachment to PDMSe and silicon substrates.

Viscosity Characterization

Viscosity measurements were conducted via rheometry to determine the critical entanglement concentration (C*) of the copolymer in solution, which in turn is used to calculate the molecular weight (MW) of the polymer. The dried copolymer was used to create a stock solution of 5.87% by weight (g/g) and diluted from there to create other solutions ranging down to 0.05%. The viscosity of each solution was measured on a Kinexus rheometer (Malvern Instruments, Ltd.) under a roughened cone and plate configuration at a shear rate of 100 Hz. Ten viscosity measurements were taken for each concentration, averaged, then plotted against the concentration on a log-log plot. The data was fit with two exponential lines and the intersection was taken as C* [1].

Chemical Composition

Attenuated total reflection Fourier transform infrared (ATR-FTIR) spectroscopy was utilized to study the chemical composition of the synthesized copolymer. A concentrated solution of 5% 1000:1 copolymer was analyzed using a Nicolet 6700 FT-IR spectrometer equipped with a ZnSe ATR crystal (Thermofisher, Waltham, Mass.). A background spectra of the ZnSe crystal and of DI water were taken separately to be subtracted out of the final spectra. One milliliter of concentrated copolymer solution was dropped onto a cleaned ATR-FTIR crystal to cover approximately ⅕ of the crystal and loaded directly into the machine. Only $115^{th}$ of the ATR crystal was covered for better spectral resolution. Scans for each spectrum were acquired with a resolution of 4 $cm^{-1}$, data spacing of 0.482 $cm^{-1}$, and maximum peak background interferogram value of 4.00±0.25. Peak fitting and spectral analyses were carried out using Nicolet OMNIC software. Prior to peak position assignments, spectra were baseline corrected. Most peaks were automatically assigned by the Nicolet OMNIC software, with 5 or less having to be manually fit due to the low intensity not being recognized by the software.

Results

A copolymer was created with the conversion rate of monomer to copolymers being approximately 80% after dialysis. Following dialysis, rotovapping, and overnight vacuum drying the final copolymer weight was 6.65 g when 8.3 g (calculated from densities and weights of AAm and VP) combined monomers were used. The initial conversion may have been higher, but only MW chains above the dialysis tubing cutoff were used in the calculation of the conversion efficiency.

Viscosity Characterization

The approximate molecular weight (MW) of the PVP-co-AAM copolymer was characterized by means of viscosity measurements as a function of copolymer solution concentration. The polymer solutions evaluated ranged in concentration from 0.05 to 5.87% (g/g). Plotting the viscosity vs concentration of solution on a log-log plot resulted in FIG. 2.2. The graph is characterized by two linear regions, the lower defining a dilute solution and the higher defining a concentrated solution. The intersection of the two linear regions serves to identify the critical entanglement (C*) value [2,3]. The C* value found in FIG. 2.2 was 1.175 $g_{polymer}/100\ g_{solution}$.

Chemical Characterization by FTIR Analysis

A solution of 5% 1000:1 PVP-co-AAM in DI water was analyzed for chemical composition using ATF-FTIR. Both the ZnSe crystal spectra and DI water spectra were subtracted from the final spectra to obtain that of only the copolymer. FIG. 2.3 shows the spectra collected with most peaks assigned. Peaks not assigned but present are listed in the caption. They were not manually labeled by the software due to their intensities being too small and were manually fit. Shown are FTIR Spectra of 1000:1 PVP-co-AAm in water. The signal from water and the ZnSe ATR crystal have been subtracted out. Peak position labels were automatically added by the software. Peaks determined manually are 1233.43 $cm^{-1}$, 685.04 $cm^{-1}$, 718.96 $cm^{-1}$, 729.57 $cm^{-1}$, and 937.5 $cm^{-1}$.

Table 2.2 gives the peak assignments for each peak position. Peak assignments were made using available literature [4,5]. Common elemental binding states found are C—C bonds, C—H bonds, C—N bonds, and C=O bonds all of which are present in PVP. Skeletal peaks for the backbone are present and noted in Table 2.2. While these skeletal peaks are dependent on the binding environment, they are not highly useful in sample qualification [5]. It is important to note that the peaks for N—H deformation from primary amides which would be present between 1620-1590 $cm^{-1}$ and around 1070 $cm^{-1}$ were not seen. These peaks would indicate the presence of PAAm monomers in a quantity greater than that of the lower detection limit of the system.

Table 2.2 shows peak assignments for 1000:1 PVP-co-AAm. The skeletal vibrations assignment encompasses peaks from 1300 to 685 $cm^{-1}$. Ring —CH2- wag and N—C stretch encompass both 1321.9 and 1376.9 $cm^{-1}$ peaks. Peak assignments were taken from Bellamy and Coates [4,5].

TABLE 2.2

Peak assignments for 1000:1 PVP-co-AAm.

| Peak Position($cm^{-1}$) | Peak Assignments | |
|---|---|---|
| 685.04 | | * |
| 692.67 | | * |
| 718.96 | —CH$_2$— rocking | * |
| 729.57 | C—C ring breathing | * |
| 937.5 | C—C ring breathing | * |
| 1003.66 | | * |
| 1019.69 | | * |
| 1174.1 | CH$_2$ ring twist | * |
| 1215.17 | | Skeletal Vibrations in C—C bonds and >CH— methyne vibrations |
| 1232.43 | —CH$_2$— twist and N—C stretch | * |

TABLE 2.2-continued

Peak assignments for 1000:1 PVP-co-AAm.

| Peak Position($cm^{-1}$) | Peak Assignments | |
|---|---|---|
| 1279.18 | | * |
| 1295.02 | ring —CH$_2$— wag and C—N strectch | * |
| 1321.93 | methyne C—H bend | Ring —CH$_2$— wag and N—C stretch |
| 1376.85 | | |
| 1425.03 | C—N stretching mode | |
| 1446.69 | methylene bend >CH— | |
| 1466.72 | —CH$_2$— bend | |
| 1497.46 | ring C—N stretch | |
| 1640.77 | carbonyl absorption band in cyclic amides >C=O stretch | |

*denotes all peaks fall in the skeletal vibrations

References, Example 2

1. Rudy, A. et al. *Lubricous Hydrogel Surface Coatings on Polydimethylsiloxane (PDMS)*. (2016).
2. Hayahara, T. & Takao, S. Relationship between polymer concentration and molecular weight in the viscosity behavior of concentrated solution. *Kolloid-Zeitschrift Zeitschrift f??r Polym.* 225, 106-111 (1968).
3. Vinogradov, G. V. & Titkova, L. V. Critical concentrations of polymers in solutions according to measurements of the viscosity and specific surface area of aerogels resulting after sublimation of the solvent. *Rheol. Acta* 7, 297-306 (1968).
4. Coates, J. in *Encyclopedia of Analytical Chemistry* (John Wiley & Sons, Ltd, 2006). doi:10.1002/9780470027318.a5606
5. Bellamy, L. J. *The Infra-red Spectra of Complex Molecules*. (Wiley and Soncs, Inc, 1975).

Example 3

Materials

PDMSe was commercially obtained in the form of a base and a curing agent (XIAMETER® RTV-4232-T2 Base Translucent and XIAMETER® T-2 Curing Agent, Dow Corning) and synthesized in a 10:1 weight ratio of base to curing agent in accordance with manufacturer's instructions [1,6]. Important to note, the PDMS used in this work is denoted with and e following the PDMS (PDMSe) acronym to denote the material is not pure polydimethyl siloxane, but an elastomer made with crosslinked PDMS and fumed silica additives which are noted to be up to 25% w/w by the manufacturer. Glutaraldehyde (GA, 50% in water), (3-aminopropyl) triethoxysilane (APTES, ≥98%), hydrogen peroxide (6% in water), and hydrochloric acid (HCl, 33%), hexamethyldisilazane (HDMS, ≥99%), were obtained from Sigma-Aldrich and used as received. Phosphate buffered saline (PBS, 1×, pH=7.4, Corning® Cellgro, Mediatech Inc.) was obtained from Fisher Scientific. DI water with a maximum 18 mΩ resistivity was generated in house using a Barnstead NanoPure™ Diamond water purification system.

Synthesis of PDMSe Substrate

PDMSe base and curing agent were mixed in a 10:1 weight ratio then degassed in a vacuum chamber for 15 minutes to remove all air bubbles. The PDMSe mixture was poured onto a glass plate treated with hexamethyldisilazane (HDMS). A 3.2 mm spacer was placed on the glass plate and the PDMSe mixture was covered by a sheet of polyurethane film. Another glass plate was placed on top of the polyurethane sheet, pressed down with a 10 lb weight to create a uniform 3.2 mm thick PDMSe sheet, and allowed to cure undisturbed for 24 hours. The PDMSe surface which was subjected to contact with the silanized side of the glass was tracked. HDMS served the purposes of creating a smooth surface with uniform hydrophobic characteristics and allowed for easy removal of the PDMSe sheet from the glass. A hydrophobic interface ensured the PDMSe would fully coat the silica additives in the base formulation leaving none exposed. If the silica additives were to be surface present, they could have represented areas that had more hydroxyl groups for attachment of the silane which could in turn have created regions of higher bonding of the copolymer resulting in a non-uniform surface. Almost all commercially available PDMSe has silica additives incorporated to increase the mechanical strength and rigidity of the final product. The exact size, geometry, and amount of silica filler is proprietary, but contact with the manufacturer gave some detail on this. This manufacturer is quoted to have used irregularly shaped high surface area fumed silica in an amount up to 25% w/w of silica in the product [5]. The polyurethane sheet was used to ease the removal of the PDMSe sheet by means of the control of interfacial energy.

Coating of PDMSe and Silicon Wafer Chips

Sheets of PDMSe were prepared for deposition by first creating 30 mm circular punches. These punches were washed with 1% Alconox solution, rinsed with deionized (DI) water, dried with compressed nitrogen, and then oxygen plasma treated in a PDC-32G Harrick plasma cleaner (Harrick Plasma Inc., Ithaca, N.Y.). The plasma cleaner was operated on a high setting (18 W) at a pressure of less than 500 mTorr using 02 bubbled through 6% hydrogen peroxide which served to increase the presence of hydroxyl groups on the PDMSe surface [1]. Single crystal silicon wafer chips were treated in the same way, however with the omission of bubbling through the hydrogen peroxide solution; the oxygen used to plasma treat the silicon chips was directly taken from the tank.

The PDMSe samples were used immediately after plasma treatment to preserve the newly created hydrophilic surface. PDMSe is known to undergo surface rearrangement to present the nonpolar species to the atmosphere [2,3]. For silicon wafer chips the timing was not critical because oxidized surface is highly stable; yet the timing was still kept constant for all substrates. The treated samples were placed in a vacuum desiccator along with 200 µl of APTES in an open dish. The desiccator was sealed and connected to a hose system joining the vacuum pump, vacuum desiccator, and a small vial of 33% HCl. The pump was turned on to evacuate the chamber to 10 Torr, then the chamber was isolated from the pump. The HCl channel was opened so HCl would vaporize and be pulled into the chamber for 30 seconds, then closed so the chamber was open again to the vacuum pump. Once a pressure of 10 Torr was reached, the tapered sleeve of the desiccator was rotated to seal it off from the hose apparatus. The hose was disconnected and the desiccator was placed in a preheated 80° C. oven for 30 minutes, after which the CVD reaction was quenched by removal from the oven and exposure to air. HCl was used to increase the reaction of APTES with the sample surface; omitting the HCl caused the PDMSe samples to turn orange after GA solution deposition.

A delay in moving the CVD chamber into the oven caused globular deposits in coating which are undesirable. Globular deposits indicated self-polymerization of APTES, rendering it unreactive to GA and therefore would decrease the attachment of copolymer gel to the substrate if present.

Samples were washed in DI water to remove excess, unreacted, and weakly bonded silanes [7]. Submersion in a solution of 2% glutaraldehyde in PBS was carried out for 2 hours at room temperature, after which the samples were washed again in copious amounts of DI water to remove excess glutaraldehyde. The silanized PDMSe substrates were promptly subjected to copolymer gel deposition.

Glutaraldehyde-treated samples were placed in individual 35 mm polystyrene petri dishes then covered with 2 ml of 5% PVP-co-AAm solution. The concentration of the polymer solution was always held above critical entanglement concentration (C*) which was found by rheometry prior to deposition. Gel attachment occurred over a minimum of 8 hours at room temperature, undisturbed. Samples were washed with DI water, stored in fresh DI water, and tribologically evaluated in PBS.

Verification of Copolymer Coverage by X-Ray Photoelectron Spectroscopy

Chemical attachment of PVP-co-AAm was verified and quantified by X-ray photoelectron spectroscopy (XPS) using treated single crystal silicon wafer chips. Silicon was used in place of PDMSe due to the tendency of oligomers and low molecular weight chains to migrate from the bulk and cover the PDMSe surface to minimize interfacial energies in the highly hydrophobic low vacuum environment of XPS [2,3]. The samples were washed in copious amounts of DI water, mounted to stainless steel platens, and dried overnight at approximately $1 \times 10^{-9}$ Torr before analysis. XPS was conducted using an Omicron XPS system (ScientiaOmicron, Taunusstein, Germany) equipped with a monochromatic Al source (1486.7 eV) and EIS-Sphera hemispherical analyzer (ScientiaOmicron, Taunusstein, Germany). Spectral measurements were carried out in a vacuum environment at approximately $2 \times 10^{-9}$ Torr. A low energy electron gun was used for surface charge neutralization to compensate for the non-conducting nature of the coating. Survey spectra were collected at 50 eV pass energy, 1 eV step sizes, 0.2 second dwell times, from a spot size of 1.74×2.75 nm. Spectra were collected at a 55 degree take off angle (ToA) corresponding to 10 nm depth. XPS spectra were quantified using CasaXPS (Casa Software Ltd.) with atomic percentages were calculated after linear background subtraction, curve fitting using a Gaussian-Lorentzian curve, integration of peak areas, and abundance correction using atomic sensitivity factors [4].

Imaging of Surface Topography by AFM

The surface topography of untreated PDMSe and treated PDMSe was imaged using a commercial MFP-3D Stand Alone AFM (Asylum Research, Santa Barbara, Calif.) under AC mode imaging. An Arrow-NC-50 sharp tip rectangular cantilever with frequency of approximately 285 kHz and a force constant of approximately 42 N/m was used. Measurements were performed on untreated samples in air, hydrated samples in PBS at room temperature, and the same hydrated sample after dehydration overnight at room temperature.

The surface topography of silicon samples was also studied to ensure the coating process was not creating massive changes in topography as this could affect friction. Silicon samples that were plasma treated, APTES coated, APTES/GA coated, and finally APTES/GA/copolymer coated were analyzed and their roughness calculated using the software used for image processing. Silicon samples were subjected to synthesis steps, rinsed with copious amounts of DI water, then dried in air at room temperature overnight before imaging.

Topographic images were processed using Scanning Probe Image Processing (SPIP™) software (Image Metrology, Denmark). Common corrections used were plane correction and absolute value correction. Plane correction accounts for sample tilt caused by mounting and can be fit automatically by the program or manually by the user. The fit used throughout this work was the automatic with a LMS of 1.

Determination of Friction Coefficient

The coefficient of friction ($\mu$) was determined using a custom built tribometer described in detail by Dunn et al. [1,8,9]. The sample was mounted to a linear reciprocating piezoelectric stage. PDMSe samples were mounted to the stage by first drying the back uncoated side and carefully placing them into 35 mm polystyrene petri dish covers by touching one edge down and applying downward force in a rolling motion with care given to not touch the coated wide with tweezers or any other objects. It was important to make sure there are no air bubbles or gaps between the PDMSe and the polystyrene dish as this allowed water to infiltrate and the sample to become detached from to the dish. If detached, the sample could float freely causing damage the tribometer probe as well as resulting in loss of data. The probe was a 3.1 mm borosilicate glass probe mounted to a dual titanium flexure cantilever having a normal and tangential force constant of 85.9 µN/µm and 72.2 µN/µm, respectively. Measurement stroke length was 800 µm, sliding velocity was 200 µm/s, and 10 cycles per spot were analyzed. Only the middle 20% of the friction loop was analyzed to negate turn around effects. An in depth description of test procedures can be found in Rudy et al. [1]. Control friction measurements were conducted on untreated PDMSe and GA/APTES coated PDMSe samples taken from the same PDMSe casting and treated at the same time. The reported detection limit of the instrument is approximately $\mu$=0.002.

Results

FIG. 3.1 depicts the attachment scheme and resulting structure of PVP-co-AAM-coated PDMSe. In short, the PDMSe substrate was plasma treated to create a hydroxylated surface (not shown in FIG. 3.1), APTES was vapor deposited then chemically bound to the substrate via thermal activation, glutaraldehyde was attached via solution deposition, and the copolymer gel was then deposited from a 5% solution of copolymer in DI water. This concentration is noted to be above C*.

Attachment scheme of PVP-co-AAm gel to PDMSe substrate using APTES and GA as linking molecules. The A and B designation on the copolymer monomeric units correlate to the relative fraction of monomers present in each chain. A and B are for vinyl pyrrolidone and acrylamide units respectively and the A:B ratio is 1000:1 in the present work.

XPS Characterization of Surfaces

Elemental characterization of the polymer-coated PDMSe surfaces by XPS provided composition of the near surface region. Survey spectra of the coated sample showed oxygen, carbon, nitrogen, and silicon present in the sample. Table 3.1 gives the calculated atomic percent of each element present at a take off angle of 55°, corresponding to a sampling depth of approximately 10 nm.

Shown in Table 3.1 is the atomic composition of 1000:1 PVP-co-AAm coated Si wafer. The percentage of each element present follows the expected trend for the attachment of PVP-co-AAm to the silicon wafer. Take off Angle (ToA) was varied to probe different depths of the surface with 55 corresponding to approximately 10 nm

TABLE 3.1

Atomic composition of 1000:1 PVP-co-AAm coated Si wafer.

| | Atomic Percentages | |
|---|---|---|
| Element | Bare Substrate | Polymer Coated Substrate |
| Oxygen | 50.1 | 25.1 |
| Carbon | 8.3 | 54.6 |
| Nitrogen | — | 5.3 |
| Silicon | 41.6 | 15.0 |

From the atomic percentages presented in Table 3.1, atomic percent silicon is observed to decrease, oxygen to decrease, carbon to increase, and nitrogen increase from bare substrate to coated substrate. This is indicative of attachment of the copolymer. The absence of other elements, like those present in the initiator and PBS (Na, Cl, P, and K from PBS [10] and Cl from AIBA), prove that the dialysis and washing steps in the overall procedure are sufficient to remove unwanted materials. A treated sample that had been washed in DI, then sonicated for 10 minutes was evaluated under XPS and served to verify that no further copolymer would come off the surface (not shown).

Further XPS tests were done to quantify the chemical changes during each step of the attachment process. A large batch of samples underwent functionalization with samples removed after APTES chemical vapor deposition, GA solution deposition, and copolymer attachment for analysis. FIG. 3.2 depicts the survey spectra for APTES treated samples, GA/APTES treated samples, and APTES/GA/copolymer treated samples (noted in the figure as PVP-co-AAm Coated). While the height of peaks in survey spectra does not exactly correspond to atomic percent, it does hold the same trend; a higher peak relative to the others signifies a higher atomic percentage of that element. Viewing FIG. 3.2, the spectra do not appreciably change between APTES treated and GA/APTES treated PDMSe substrates. The noticeable change is the reduction in nitrogen peak height, which is expected as the nitrogen comes from APTES and should be attenuated with the addition of GA on top. Total attenuation is not seen though which can be explained by the size of GA. GA molecules alone are less than 10 nm in length and even if there were a theoretically completely dense layer, it is unreasonable to think the GA would be standing on end. This could also be partially contributing to non-ideal coverage, either from APTES self bonding or GA bonding to two APTES molecules and nullifying the functionality of both molecules. Important to note next is the change from GA/APTES functionalized samples to copolymer coated samples. Here the silicon signal is attenuated, the carbon to oxygen ratio increases, and the nitrogen signal increases. The nitrogen signal increases as a result of copolymer attachment. The silicon signal is attenuated, showing that there is material covering the substrate but not totally attenuated which would be indicative of a full coverage coating. The cause for the lack of total attenuation is elucidated with AFM results discussed further in the discussion. The significance of the increasing carbon to oxygen ratio is a large amount of oxygen signal is coming from the substrate which is then covered by the carbon rich polymer; proving coverage of the substrate.

Shown in FIG. 3.2 are XPS survey spectra of treatment steps using in attachment of the copolymer to a substrate. Each survey has a representation of the added molecule. Each subsequent step adds onto the former step. The first step is the lowest spectra and the last is the uppermost in the figure.

Surface Topography and Roughness

Tapping mode AFM was employed to study the topography of both uncoated and copolymer coated PDMSe samples along with all synthesis steps conducted on silicon wafers. Uncoated PDMSe samples were imaged in air, while polymer coated PDMSe samples were imaged in both air and in an aqueous environment. All silicon samples were imaged in air. Untreated PDMSe height images taken by AFM show vast differences in the base material topography.

Untreated PDMSe samples were taken from regions of the same PDMSe casting approximately 3 inches apart, washed in 1% Alconox solution, and rinsed in DI water followed by an ethanol rinse. The samples were handled at the same time in the exact same manner. They were then dried with a blast of compressed nitrogen before being loaded into the AFM for AC mode analysis. FIGS. 3.3 and 3.4 show the two different uncoated samples, each a 5×5 μm scan. The total height amplitude for untreated PDMSe sample 1 is 80 nm while sample 2 is only 10 nm. This great difference in surface topography is most likely caused by differences in surface chemistry or topography of the cast-against surface. Sample 2 was taken from near the edge of the casting and sample 1 was taken closer to the center. The cast-against surface is homogenous, being a sheet of plate glass uniformly covered with HDMS silane. Even though the casting process used spacers to create a uniform thickness, the edges of the casting tended to be slightly thinner than the middle. Shrinkage during curing [11] could have caused the edges to slightly pull away from the glass casting surface leaving parts to finish curing in free space, thus creating the altered topography between the samples. AFM height image of untreated PDMSe sample 1 is shown in FIG. 3.3 and sample 2 is shown in FIG. 3.4. Height amplitude, being the maximum z-scale height minus the minimum z-scale height, is approximately 80 nm over the 5 um scan area for sample 1 and only 10 nm for sample 2.

Shown in FIG. 3.5 are tapping mode height AFM images of hydrated (A and B) and dehydrated (C) copolymer coated PDMSe. Image A is a 4×4 μm scan in the hydrated state. Image B and C are 500 nm×500 nm images in the hydrated and dehydrated state respectively. The grayscale bars to the right of each image correspond to the height of the colors in the image. The dehydrated image has distinct depressions seen as dark spots. These are not present in the hydrated sample image at either magnification.

The topographic images of silicon samples were of secondary importance to the roughness values garnered from those images as the roughness of PDMSe substrates is much higher than that of silicon. The goal in measuring the topography of silicon wafers was to verify the coating process did not introduce large topographic features which would increase the coefficient of friction. Table 3.2 gives roughness values for each synthesis step on silicon. As would be expected, the roughness for plasma treated silicon is extremely smooth at 0.08 nm. Coating with APTES caused the roughness to increase to 0.29, which is an order of magnitude higher, but still a very flat surface. Further coating with GA did not significantly increase the roughness as indicated with a roughness value of 0.27 nm. Final coating with the copolymer caused the roughness to increase to 0.67 nm. Again, this is a significant increase, but is still considered a smooth surface. This proves the coating processes did not themselves create a rough surface which would contribute to an increase in friction due to topography changes.

TABLE 3.2

Roughness values for all synthesis steps on silicon in units of nm.

| Sample | Average Roughness (nm) |
| --- | --- |
| Plasma Cleaned Si | 0.0836 |
| APTES Coated | 0.299 |
| GA Coated | 0.278 |
| PVP-co-AAm Coated | 0.683 |

Tribological Characterization

The coefficient of friction of the polymer surfaces was measured over 800 microns with a reciprocating microtribometer employing a borosilicate bead as the counter face. Measurements of friction force vs normal force were taken on uncoated PDMSe, APTES/GA coated PDMSe, and gel coated PDMSe. The CoF values were 2.8 for uncoated PDMSe, 0.25 for APTES/GA coated PDMSe, and 0.073 for copolymer coated PDMSe. Testing of APTES/GA coated PDMSe verified the vast reduction in friction was indeed coming from the copolymer gel, and not simply from APTES and GA. All samples were run against a glass probe immersed in approximately 2 ml of PBS. The plot of friction force ($F_f$) vs normal force ($F_n$) is shown in FIG. 3.6 and CoF values are presented in Table 3.3. Standard deviation for GA coated and PVP-co-AAm coated are 0.01 and 0.003 respectively. The plot of $F_f$ vs $F_n$ was created by measuring multiple friction loops at each normal force. The coefficient of friction was determined from the friction loops, averaged, and plotted against the $F_n$ each friction measurement was taken at to result in FIG. 3.6. The slope each line is the CoF independent of probe-sample adhesion or repulsion forces. Detailed explanation can be found in Rudy et al.

TABLE 3.3

CoF values for treated PDMSe and uncoated PDMSe.

| Sample Type | Coefficient of Friction (μ) |
| --- | --- |
| Uncoated PDMSe | 2.8 |
| GA Coated PDMSe | 0.25 |
| PVP-co-AAm Coated PDMSe | 0.073 |

Shown in FIG. 3.6 is a graph of Friction Force vs Normal Force for untreated PDMSe, GA/APTES treated PDMSe, and PVP-co-AAm coated PDMSe. Linear equations were fit to each data set, with the slope of the equation being the coefficient of friction. Non-zero intercepts represent adhesion (positive) or repulsion (negative) between the surface and the glass probe. The error bars present are smaller than the data markers used and represent the average standard deviation from 9 samples for each sample type and each normal force. The error bars can be seen within the circle markers for the PVP-co-AAm Coated samples.

References, Example 3

1. Rudy, A. et al. *Lubricous Hydrogel Surface Coatings on Polydimethylsiloxane (PDMS)*. (2016).
2. Fukazawa, K. & Ishihara, K. Simple surface treatment using amphiphilic phospholipid polymers to obtain wetting and lubricity on polydimethylsiloxane-based substrates. *Colloids Surfaces B Biointerfaces* 97, 70-76 (2012).
3. Ellis, A. V & Voelcker, N. H. Recent Developments in PDMS Surface Modification for Microfluidic Devices modification for microfluidic devices. *Electrophoresis* (2010). doi:10.1002/elps.200900475
4. Moulder, J., Stickle, W., Sobol, P. & Bomben, K. *Handbook of X-ray Photoelectron Spectroscopy*. (ULVAC-PHI, Inc, 1992).
5. De Jaeger, R. & Gleria, M. *Inorganic Polymers*. (Nova Science Publishers, 2007).
6. Urueña, J. M. et al. Mesh Size Control of Polymer Fluctuation Lubrication in Gemini Hydrogels. *Biotribology* 1-2, 24-29 (2015).
7. Smith, Smith, E. A. & Chen, W. How to prevent the loss of surface functionality derived from aminosilanes. *Langmuir* 24, 12405-12409 (2008).
8. Dunn, A. C., Sawyer, W. G. & Angelini, T. E. Gemini interfaces in aqueous lubrication with hydrogels. *Tribol. Lett.* 54, 59-66 (2014).
9. Rennie, A. C., Dickrell, P. L. & Sawyer, W. G. Friction coefficient of soft contact lenses: measurements and modeling. *Tribol. Lett.* 18, 499-504 (2005).
10. Phosphate Buffered Saline Product Description. (2017). Available at: http://cellgro.com/phosphate-buffered-saline-1x-2.html. (Accessed: 2 Jun. 2017)
11. Colas, A. *Silicones: Preparation, Properties and Performance*. (2005).

Example 4

Materials

Hydrochloric acid (HCl, 33%), (3-aminopropyl)triethoxysilane (APTES, ≥98%), glutaraldehyde (GA, 50% in water), acrylamide (AAm, 99%), hexamethyldisilazane (HDMS, ≥99%), 2,2'-azobis(2-methylpropionamidine) dihydrochloride (MBA, 97%) and 1-vinyl-2-pyrrolidone (VP, ≥99%), were obtained from Sigma-Aldrich and used as received. PDMSe was obtained from a commercial source in the form of a curing agent and base (XIAMETER® RTV-4232-T2 Base Translucent and XIAMETER® T-2 Curing Agent, Dow Corning) and combined in a 10:1 ratio in accordance with the manufacturer's instruction to create crosslinked PDMSe sheets. Phosphate buffered saline (PBS, 1×, pH=7.4, Corning® Cellgro, Mediatech Inc.) was obtained from Fisher Scientific and used as received as the liquid environment for friction experiments. DI water with a maximum 18 mΩ resistivity was generated in house using a Barnstead NanoPure™ Diamond water purification system.

Synthesis of Varying Monomer Ratio and Molecular Weight Copolymers

Linear high molecular weight copolymer chains of poly(vinylpyrrolidone-co-acrylamide) were created by solution free radical polymerization. Three different monomeric ratios were created using the same polymerization conditions and times. These 10:1, 100:1, and 1000:1 formulations are coined "ratio formulations" for clarity.

TABLE 4.1

List of component amounts for various monomer ratio copolymers in moles of each substance.

| Component | 1000:1 | 100:1 | 10:1 |
|---|---|---|---|
| Vinyl Pyrrolidone | $7.38 \times 10^{-3}$ | $7.38 \times 10^{-3}$ | $7.38 \times 10^{-3}$ |
| Acrylamide | $0.0747 \times 10^{-3}$ | $0.747 \times 10^{-3}$ | $7.47 \times 10^{-3}$ |
| AIBA | $22.125 \times 10^{-5}$ | $22.125 \times 10^{-5}$ | $22.125 \times 10^{-5}$ |
| DI $H_2O$ | 9.66 | 9.66 | 9.66 |

For various monomeric ratio polymers, the VP concentration was held constant while the amount of AAm was increased. This was done to preserve the volume of total solution and molality of all constituents except AAm. Changing the amount of VP would change the amount of DI water needed, and could potentially have an impact on polymerization gradients and concentrations. Table 4.1 lists the amounts of all components used in synthesis of the three different copolymer ratios. The 1000:1 formulation was used in measurements.

Copolymers of varying molecular weight were synthesized via solution free radical polymerization using the 100:1 formulation. The only divergence is a change in the amount of initiator employed. By changing the amount of initiator, more polymers are started in the beginning thereby decreasing the total amount of monomer available for each started chain. This leads to a reduction in total length of the linear polymer. Table 4.2 lists the amounts of all components used in synthesis of the three molecular weight polymers. Polymers will be referred to as A, B, and C formulations, corresponding to the amount of initiator used, 60, 120, and 180 mg, respectively. The monomeric ratio was held constant at 100:1 to simplify tests and negate any further convolution of results due to changing polymerization conditions.

TABLE 4.2

List of component amounts for various molecular weight copolymers given as moles of each substance.

| Component | A | B | C |
|---|---|---|---|
| Vinyl Pyrrolidone | $7.38 \times 10^{-3}$ | $7.38 \times 10^{-3}$ | $7.38 \times 10^{-3}$ |
| Acrylamide | $0.0747 \times 10^{-3}$ | $0.0747 \times 10^{-3}$ | $0.0747 \times 10^{-3}$ |
| AIBA | $22.125 \times 10^{-5}$ | $44.25 \times 10^{-5}$ | $66.375 \times 10^{-5}$ |
| DI $H_2O$ | 9.66 | 9.66 | 9.66 |

For the polymerization reaction, reactants were added to a flask and nitrogen purged for 2 hours to remove any oxygen as oxygen serves as a free radical scavenger. The reaction flask was supported in a 60° C. water bath and run for four hours, then quenched by exposure to air. The resulting copolymers were dialyzed for three days, dried using rotary evaporation, and reconstituted with water to create concentrated stock solutions.

Molecular Weight Determination

The molecular weights of all polymers created was determined. The dried copolymer was used to create a stock solution (varying for each polymer but always over 10%) and diluted from there to create other solutions ranging down to 0.05%. The viscosity of each solution was measured on a Kinexus rheometer (Malvern Instruments, Ltd.) under a roughened cone and plate configuration at a shear rate of 100 Hz. Ten viscosity measurements were taken for each concentration, averaged, then plotted against the concentration on a log-log plot. The data was fitted with two exponential lines and the intersection was taken as C*

Chemical Characterization of Copolymers

Attenuated total reflection Fourier transform infrared (ATR-FTIR) spectroscopy was utilized to study the chemical composition of the copolymers with varying monomeric ratios. Copolymers B and C were not evaluated under FTIR because they should have the same atomic ratios since the prepolymerization solutions were the same other than the initiator which accounts for less than 1%. This 1% is less than the detection limit for the system used and therefore would not register a difference between A, B, and C formulations. Solutions of 5% of the ratio formulations were analyzed using a Nicolet 6700 FT-IR spectrometer equipped with a ZnSe ATR crystal (Thermofisher, Waltham, Mass.). Spectra of the ZnSe crystal and of DI water were taken first to subtract out of the final spectra. One milliliter of concentrated copolymer solution was dropped onto a cleaned ATR-FTIR crystal to cover approximately $115^{th}$ of the crystal and loaded directly into the machine. Only $115^{th}$ of the ATR crystal was covered for better spectral resolution. Scans for each spectrum were acquired with a resolution of 4 cm$^{-1}$, data spacing of 0.482 cm$^{-1}$, and maximum peak background interferogram value of 4.00±0.25. Peak fitting and spectral analysis were carried out using Nicolet OMNIC software. Prior to peak position assignments, spectra were baseline corrected using the ZnSe crystal and DI water spectra. Most peaks were automatically assigned by the Nicolet OMNIC software, with 5 or less having to be manually fit due to the low intensity not being recognized by the software.

Attachment to PDMSe Substrates

Sheets of PDMSe were prepared by mixing the Xiamater PDMSe base and curing agent in a 10 to 1 ratio, degassing in a vacuum chamber for 15 minutes, and casting this between a HDMS treated glass plate and polyurethane sheet with 3.2 mm spacers. Samples were prepared by punching out 30 mm diameter rounds from the sheets which were washed with 1% Alconox solution, rinsed with deionized (DI) water, and dried with compressed nitrogen. The PDMSe punches then were oxygen plasma treated in a PDC-32G Harrick plasma cleaner (Harrick Plasma Inc., Ithaca, N.Y.) operated on a high setting (18 W) at a pressure of less than 500 mTorr using O2 bubbled through 6% hydrogen peroxide serving to increase the presence of hydroxyl groups on the PDMSe surface [1]. Single crystal silicon wafer chips were treated in the same way apart from the omission of oxygen gas bubbling through the hydrogen peroxide solution; the oxygen used to plasma treat the silicon chips was used directly from the tank.

Samples were used immediately after plasma treatment of the surface to preserve the newly created hydrophilic character as the PDMSe is known to surface rearrange in a relatively short time frame [2,3,13]. The treated samples were placed in a vacuum desiccator along with 200 µl of APTES in an open dish. The desiccator was sealed and connected via a hose system joining the vacuum pump, vacuum desiccator, and a small vial of 33% HCl. The pump was turned on to evacuate the chamber to 10 Torr. The desiccator was then isolated from the pump and the HCl channel opened for 30 seconds, which caused HCl vapor to enter the system. The HCl channel was closed and the vacuum pump was turned onto evacuate the desiccator to 10 Torr again. Once this was reached, the tapered sleeve of the desiccator was rotated to seal it off from the hose, the hose was disconnected, and the desiccator was placed immediately in a preheated 80° C. oven for 30 minutes. The CVD reaction was quenched by removal from the oven and exposure of the sample to air.

The silanized samples were washed in DI water to remove excess, unreacted, and weakly bonded silanes [10]. Submersion in a solution of 2% glutaraldehyde in PBS was carried out for two hours at room temperature, after which the samples were washed again in copious amounts of DI water to remove excess glutaraldehyde. The silanized PDMSe substrates were promptly subjected to copolymer gel deposition by placing sample in individual 35 mm polystyrene petri dishes and fully covered with 2 mL of 5% PVP-co-AAm solution. The concentration of the polymer solution was always held above the critical entanglement concentration (C*) of all copolymers created. Gel attachment occurred over a minimum of 8 hours at room temperature, undisturbed. Samples were washed with DI water and tribologically evaluated in PBS.

A total of 5 different copolymers were used in this study. Three formulations of various monomeric ratios, 1000:1, 100:1, and 10:1, and three of various molecular weight, labeled A, B, and C (Table 4.2) were attached and tested. Copolymer A and the 100:1 copolymer are the same formulation.

Chemical Characterization of Varying Monomeric Ratio Copolymer Coated Substrates Attachment of PVP-co-AAm coatings onto substrates was verified and quantified by XPS using silicon wafers as the sample substrates. Samples were washed in copious amounts of DI water before analysis to remove any unbound copolymer. An Omicron XPS system (ScientiaOmicron, Taunusstein, Germany) equipped with a monochromatic Al source (1486.7) and EIS-Sphera hemispherical analyzer (ScientiaOmicron, Taunusstein, Germany) was used. Measurement took place at approximately $2\times10^{10}$ Torr. Surface charge neutralization was necessary due to the nonconductive nature of the coating. A low energy electron gun (CN 10 charge neutralization system, Omicron Nanotechnology. Taunusstein, Germany) was used for this purpose. Survey spectra were collected at 50 eV pass energy, 1 eV step size, and 0.2 s dwell time. Spectra were analyzed using CasaXPS (Casa Software Ltd.) for curve fitting and background subtraction. Silicon was used as the substrate due to the tendency of low molecular weight chains and oligomers migrating from the bulk of PDMSe samples to the outermost surface in vacuum [2,3] which would obscure the spectra of the true surface.

Frictional Dependence

The coefficient of friction was determined using a custom built tribometer described in detail by Dunn et al. [1,11,12]. The probe was a 3.1 mm borosilicate glass probe mounted to a dual titanium flexure cantilever having a normal and tangential force constant of 85.9 µN/µm and 72.2 µN/µm, respectively. The sample was mounted to a stage that was linearly reciprocated with a measurement stroke length 800 µm and sliding velocity of 200 µm/s. PDMSe samples were mounted to the stage by first drying the back, uncoated side and carefully placing them into 35 mm polystyrene petri dish covers by touching one edge down and applying downward force in a rolling motion with care given to not touch the coated side with tweezers or any other objects. It is important to make sure there are no air bubbles or gaps between the PDMSe and the polystyrene dish as this allows water to infiltrate and the sample to become detached from to the dish. If detached, the sample can float freely causing damage to the tribometer probe as well as resulting in loss of data. Data sets were recorded as normal force vs. frictional force where the middle 20% of the friction loop was analyzed to negate turn around effects. The frictional force at multiple normal forces (500, 750, 1000, 1250, 1750, and 2000 µN of force) was measured to create plots used to calculate CoF values. An in depth description of test procedures can be found in Rudy et al. [1]. The detection limit of the instrument is approximately µ=0.002. All experiments were conducted in PBS at STP and the probe was cleaned between samples using an ethanol soaked laboratory wipe.

Results

Molecular Weight of Varying Copolymers

The viscosity of measured solutions was plotted against the concentration on a log-log plot creating two distinct linear regions. It is the intersection of these lines that corresponds to C* [1,5,14]. Shown in FIG. 4.1 is the viscosity vs. concentration data for the 10:1, 100:1, and 1000:1 formulations. Solutions were made by mixing the copolymer in DI water. Solutions were measured at 25° C., controlled by the rheometer. The point of intersection of the two lines gives the critical entanglement concentration for the polymer. Lines were fit using Excels least squares fit to power functions.

Table 4.3 gives the C* value, molecular weight, and radius of gyration for all formulations of copolymer calculated using Equations 1.2 and 1.3 [1,8,9]. The formulation for 100:1 and A are the same. The formula relating these values is Equation 1.2. The molecular weight for 10:1, 100:1, and 1000:1 are 130.650 kDa, 154.5 kDa, and 140.3 kDa respectively. These are relatively close to one another indicating no trend can be seen relating MW to monomer ratio. The molecular weights of A B and C formulations are 154,500 Da, 48,800 Da, and 36,000 Da respectively proving the change in initiator was successful in creating various MW of the same formulation.

TABLE 4.3

Critical entanglement concentration, calculated molecular weight, and radius of gyration for all copolymer formulations.

| Monomer Ratio | C* | MW | Rg (nm) |
|---|---|---|---|
| 10:1 | 1.24 | 130,650 | 16.1 |
| 100:1 (Copolymer A)* | 1.09 | 154,500 | 17.8 |
| 1000:1 | 1.175 | 140,304 | 16.7 |
| Copolymer B | 2.63 | 48,800 | 9.0 |
| Copolymer C | 3.31 | 36,000 | 7.5 |

*Copolymer A is the same formulation as the 100:1 copolymer

Chemical Characterization of Copolymers

Ratio formulation copolymer solutions of 5% concentration in DI water were analyzed for chemical composition using ATF-FTIR. Both the ZnSe crystal spectra and DI water spectra were subtracted from the final spectra to obtain that of only the copolymer. Shown in FIG. 4.2 is a plot of FTIR spectra of the three various monomeric ratio copolymers. All spectra have had water and the ZnSe crystal subtracted out as well as plotted on a common axis. The arrow and highlighted section correspond to the only difference seen in spectra at 1073.91 cm$^{-1}$. FIG. 4.2 shows the spectra collected for all solutions on a common x-axis with the highlighted peak being the only noticeable difference the samples. The 10:1 and 100:1 copolymers have a peak at 1073.9 cm$^{-1}$ corresponding to N—C stretch in primary amines where the 1000:1 spectra did not. Peaks positions and assignments for all spectra are shown in Table 4.4. Main peak positions were automatically selected by the OMNIC software while very small peaks were not recognized by the software due to their intensities being too small. Commonalities found include assignments for C—C bonds, C—H bonds, C—N bonds, and C=O bonds. Skeletal peaks for the backbone are present and noted in Table 4.4. While these skeletal peaks are dependent on the binding environment, they are not highly useful in sample qualification [7].

Shown in Table 4.4 are peak assignments for 1000:1, 100:1, and 10:1 PVP-co-AAm copolymers ATR-FTIR spectra after subtraction of the ATR crystal and DI water. The skeletal vibrations assignment encompasses peaks from 1300 to 685 cm$^{-1}$ and are denoted in the table with an asterisk. Ring —CH2- wag and N—C stretch encompass both 1321.9 and 1376.9 cm$^{-1}$ peaks. Peak assignments were taken from Bellamy and Coates [6,7].

TABLE 4.4

Peak assignments for 1000:1, 100:1, and 10:1 PVP-co-AAm copolymers ATR-FTIR spectra after subtraction of the ATR crystal and DI water.

| Peak Positions for Various Copolymer Monomeric Ratios | | | | |
|---|---|---|---|---|
| 1000 to 1 | 100 to 1 | 10 to 1 | Peak Assignments | |
| 685.04 | 686.65 | 686.65 | | Skeletal Vibrations in C—C bonds and >CH— methyne vibrations |
| 692.67 | 692.67 | 692.67 | | |
| 718.96 | 718.43 | 718.43 | —CH2— rocking | |
| 729.57 | 729.57 | 729.57 | C—C ring breathing | * |
| 937.5 | 937.5 | 937.5 | C—C ring breathing | * |
| 1003.66 | 1003.5 | 1003.71 | | * |
| 1019.69 | 1020.29 | 1020.32 | | * |
| — | 1073.65 | 1073.91 | C—N stretch in amide | * |
| 1174.1 | 1173.83 | 1173.27 | CH2 ring twist | * |
| 1215.17 | 1216.18 | 1216.19 | | * |
| 1232.43 | 1233.433 | 1233.487 | CH2 twist and N—C stretch | * |
| 1279.18 | 1278.8 | 1276.72 | | * |
| 1295.02 | 1295.07 | 1295.07 | CH2 ring wag and C—N stretch | * |
| 1321.93 | 1321.8 | 1321.8 | C—H methyne bend | C—H bend + Ring CH2 wag + NC stretch |
| 1376.85 | 1375.81 | 1375.14 | | |
| 1425.03 | 1424.94 | 1424.95 | N—C stretching mode | |
| 1446.59 | 1446.88 | 1446.92 | C—H methylene bend | |
| 1466.72 | 1466.41 | 1466.43 | —CH2— bend | |
| 1497.46 | 1496.78 | 1496.64 | C—N ring stretch | |
| 1640.77 | 1640.34 | 1640.21 | C=O carbonyl stretch absorption band in cyclic amides | |

*denotes all peaks fall in the skeletal vibrations

FTIR results confirm expected elemental presence of C—C, C—H, C—N, and C=O bonds in all copolymers. The peak located at 1073.9 cm$^{-1}$ which is attributed to N—C stretch in primary amines was only seen in the 100:1 and 10:1 copolymers. This is not unexpected as the detection limit for the system is approximately 1% so the acrylamide unit making up only 0.1% in the 1000:1 copolymer would not be seen. The presence of this N—C stretch peak verifies acrylamide was successfully incorporated into the copolymer.

Chemical Characterization of Coated Silicon Substrates

Employment of XPS at a ToA of 55° gives the composition of surfaces at approximately 10 nm depth for a predominantly carbon based film. XPS was carried out on the three different ratio formulations but not A, B, and C formulations. This was because A, B, and C copolymers should have the same composition. Background subtraction and curve fitting were applied to the core level spectra then sensitivity factors were applied to integrated peak areas giving the elemental compositions listed in Table 4.5. Survey spectra included only oxygen, carbon, nitrogen, and silicon, as expected. As the amount of AAm in the copolymer increases, the amount of nitrogen decreases, oxygen increases, carbon decreases and silicon increases. The absence of other elements, like those present in PBS, prove that the dialysis and washing steps in the overall procedure are sufficient to remove unwanted materials. A treated sample that had been washed in DI, then sonicated for 10 minutes was evaluated under XPS verified no further copolymer would come off the surface (not shown). Referencing the monomers in FIG. 2.1, XPS of pure polymers would give atomic percentages of 60% carbon, 20% oxygen, and 20% nitrogen in PAAm and 75% carbon, 12.5% oxygen, and 12.5% nitrogen in PVP for bulk polymer in an ideal system. These values are calculated as the number of atoms of each element divided by the total number of atoms. Hydrogen is not accounted for because XPS cannot detect hydrogen or helium and it is therefore not computed in the atomic percentages displayed [4,15]. So with increasing PAAm in the copolymer one would expect an increase in oxygen and nitrogen signal with a decrease in carbon signal. This is not consistent with what is seen in the data and nitrogen is the only signal that follows the expected trend. The observed trends are rationalized in a following section.

TABLE 4.5

Atomic percentages of elements present in XPS scans for various monomeric ratio copolymers. All spectra were taken at a 55° take of angle.

| | Sample | | |
|---|---|---|---|
| Element | 10 to 1 | 100 to 1 | 1000 to 1 |
| O | 23.4 | 23.3 | 28.0 |
| C | 54.4 | 54.0 | 46.1 |
| N | 6.4 | 5.2 | 4.5 |
| Si | 15.8 | 17.5 | 21.4 |

Friction Response

The CoF of the copolymer coated PDMSe surfaces was measured using a reciprocating motion over 800 μm and slid against a 3.1 mm borosilicate sphere with PBS as the surrounding liquid environment. Measurements of friction force vs. normal force for multiple normal force values were plotted and fit linearly with a slope which corresponds to the CoF. FIG. 4.3 provides the $F_f$ vs $F_n$ plots for the different monomeric ratio and molecular weight copolymers. The results are depicted in plots of friction force vs. normal force for all monomeric variation copolymers (left) and all molecular weight variation copolymers (right). The slope of the linear fits are the CoF values for each copolymer. Each data set is the average of nine distinct sampling spots. CoF values for ratio formulations and varying MW formulations are represented in Table 4.6 and Table 4.7. In Table 4.6, each value reported is an average of 3 spots on 3 separate samples with ten friction loops were taken for each spot. In Table 4.7, all copolymers have the same monomer ratio of 100:1. FIG. 4.4 plots the CoF against molecular weight of the copolymers A, B, and C. The standard deviation values are shown as error bars. All copolymers have the monomeric ratio of 100:1.

TABLE 4.6

CoF values for ratio formulations of copolymers corresponding to various monomeric ratios.

| Monomer Ratio | CoF | Stdev of CoF |
|---|---|---|
| 10:1 | 0.085 | 0.031 |
| 100:1 | 0.040 | 0.007 |
| 1000:1 | 0.076 | 0.012 |

TABLE 4.7

CoF values and their standard deviations for different molecular weight copolymers A, B, and C, and the corresponding MW.

| Copolymer | Molecular Weight | CoF | Stdev of CoF |
|---|---|---|---|
| A | 154,500 | 0.040 | 0.007 |
| B | 48,800 | 0.086 | 0.021 |
| C | 36,000 | 0.23 | 0.006 |

From the plot of $F_n$ and $F_f$ in FIG. 4.3, it can be seen that the monomeric ratio does not have a direct effect on the CoF values, which are the slopes of the linear fits of the data. The 100:1 copolymer has the lowest friction, with the slopes for the 1000:1 and 10:1 being indistinguishable to the eye. Students t-test were run to prove the 1000:1 and 10:1 CoF values were indistinguishable from one another, but different than the 100:1 copolymer. The p-value results are listed in Table 4.8. Generally, a p-value of 0.05 or less signifies the two means are statistically different from each other using our null hypotheses. Looking to Table 4.8, it is seen that comparing 10:1 and 1000:1 gives a p-value of 0.38 which signifies that these values are statistically indistinguishable from one another, while the 100:1 copolymer is significantly different from both the 10:1 and the 1000:1 copolymers with p-values of 0.0035 and 0.0000135.

TABLE 4.8

P-values from students two tailed T-Test comparing CoF values between coatings using varying monomeric ratio copolymer coatings

| Monomeric Ratio of Copolymer compared | P value |
|---|---|
| 10:1 to 100:1 | 0.0035 |
| 10:1 to 1000:1 | 0.38 |
| 100:1 to 1000:1 | 0.0000135 |

The values in Table 4.7 as well as the plot of MW vs CoF and the FIG. 4.4 and $F_f$ vs $F_n$ plot used to quantify Cof in FIG. 4.3 all illustrate a distinct inverse relationship between CoF and molecular weight of the polymer. An increase in molecular weight of the copolymer results in a decrease in the CoF. As only three molecular weights were tested, neither a full governing equation nor numeric proportionality can be determined. The physical basis for this relationship is proposed in the following section.

References, Example 4

1. Rudy, A. et al. *Lubricous Hydrogel Surface Coatings on Polydimethylsiloxane (PDMS)*. (2016).
2. Fukazawa, K. & Ishihara, K. Simple surface treatment using amphiphilic phospholipid polymers to obtain wetting and lubricity on polydimethylsiloxane-based substrates. *Colloids Surfaces B Biointerfaces* 97, 70-76 (2012).
3. Ellis, A. V & Voelcker, N. H. Recent Developments in PDMS Surface Modification for Microfluidic Devices modification for microfluidic devices. *Electrophoresis* (2010). doi:10.1002/elps.200900475
4. Stojilovic, N. Why Can't We See Hydrogen in X-ray Photoelectron Spectroscopy? *J. Chem. Educ.* 89, 1331-1332 (2012).
5. Hayahara, T. & Takao, S. Relationship between polymer concentration and molecular weight in the viscosity behavior of concentrated solution. *Kolloid-Zeitschrift Zeitschrift f??r Polym.* 225, 106-111 (1968).
6. Coates, J. in *Encyclopedia of Analytical Chemistry* (John Wiley & Sons, Ltd, 2006). doi:10.1002/9780470027318.a5606
7. Bellamy, L. J. *The Infra-red Spectra of Complex Molecules*. (Wiley and Soncs, Inc, 1975).
8. Liu, Y., Jun, Y. & Steinberg, V. Concentration dependence of the longest relaxation times of dilute and semi-dilute polymer solutions. *J. Rheol.* (N. Y. N. Y). 53, 1069-1085 (2009).
9. Odell, J. A. & Haward, S. J. Viscosity enhancement in the flow of hydrolysed poly(acrylamide) saline solutions around spheres: Implications for enhanced oil recovery. *Rheol. Acta* 47, 129-137 (2008).
10. Smith, Smith, E. A. & Chen, W. How to prevent the loss of surface functionality derived from aminosilanes. *Langmuir* 24, 12405-12409 (2008).
11. Dunn, A. C., Sawyer, W. G. & Angelini, T. E. Gemini interfaces in aqueous lubrication with hydrogels. *Tribol. Lett.* 54, 59-66 (2014).
12. Rennie, A. C., Dickrell, P. L. & Sawyer, W. G. Friction coefficient of soft contact lenses: measurements and modeling. *Tribol. Lett.* 18, 499-504 (2005).
13. Larson, B. J. et al. Long-term reduction in poly(dimethylsiloxane) surface hydrophobicity via cold-plasma treatments. *Langmuir* 29, 12990-12996 (2013).
14. Fetters, L. Determination of the intermolecular entanglement coupling spacings in polyisoprene by viscosity measurements. *J. Res. Natl. Bur. Std A* 69, 33-37 (1965).
15. Briggs, D. *Handbook of X-Ray and Ultraviolet Photoelectron Spectroscopy. Handbook of X-Ray and Ultraviolet Photoelectron Spectroscopy* (1977). doi:10.1002/piuz.19790100107

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:
1. A method of making a lubricious structure, comprising:
providing a substrate with a surface;
synthesizing a physically entangled polymer network, wherein a mesh size of the physically entangled network of polymers is about 5.5 to 8 nm; and
reacting the physically entangled polymer network with the surface of the substrate to form a coating on the surface of the substrate to form the lubricious structure.
2. The method of claim 1, wherein synthesizing the physically entangled polymer network comprises free radical polymerization under an inert nitrogen atmosphere.
3. The method of claim 1, wherein synthesizing the physically entangled polymer network comprises mixing acrylamide groups and acrylic groups, prior to reacting with the surface of the substrate, with a ratio of about 10:1.
4. The method of claim 1, wherein synthesizing the physically entangled polymer network comprises dialysis in de-ionized H2O.
5. The method of claim 1, wherein synthesizing the physically entangled polymer network comprises drying the physically entangled polymer network in a vacuum chamber.

* * * * *